(12) United States Patent
Karmarkar et al.

(10) Patent No.: US 7,725,161 B2
(45) Date of Patent: May 25, 2010

(54) ACTIVE MRI INTRAMYOCARDIAL INJECITON CATHETER WITH A DEFLECTABLE DISTAL SECTION

(75) Inventors: Parag V. Karmarkar, Columbia, MD (US); Ergin Atalar, Columbia, MD (US)

(73) Assignee: John Hopkins University, Baltimore, MD (US)

( * ) Notice: Subject to any disclaimer, the term of this patent is extended or adjusted under 35 U.S.C. 154(b) by 1212 days.

(21) Appl. No.: 10/769,994

(22) Filed: Feb. 3, 2004

(65) Prior Publication Data

US 2004/0220470 A1 Nov. 4, 2004

Related U.S. Application Data

(60) Provisional application No. 60/444,430, filed on Feb. 3, 2003.

(51) Int. Cl.
*A61B 5/055* (2006.01)
(52) U.S. Cl. .................. 600/423; 600/407; 600/410; 600/421; 600/422; 600/424
(58) Field of Classification Search .............. 600/407, 600/410, 421–423, 424, 433, 434, 435; 604/264, 604/95.01; 607/122; 324/318, 322
See application file for complete search history.

(56) References Cited

U.S. PATENT DOCUMENTS

| 4,898,577 | A | 2/1990 | Badger et al. |
| 5,030,204 | A | 7/1991 | Badger et al. |
| 5,487,757 | A | 1/1996 | Truckai et al. |
| 5,699,801 | A | 12/1997 | Atalar et al. |
| 5,755,760 | A | 5/1998 | Maguire et al. |
| 5,792,055 | A * | 8/1998 | McKinnon ............ 600/410 |
| 5,928,145 | A * | 7/1999 | Ocali et al. ............ 600/410 |
| 5,980,516 | A | 11/1999 | Mulier et al. |
| 6,004,269 | A * | 12/1999 | Crowley et al. ........ 600/439 |
| 6,004,295 | A | 12/1999 | Langer et al. |
| 6,102,887 | A | 8/2000 | Altman |
| 6,198,974 | B1 | 3/2001 | Webster, Jr. |
| 6,210,362 | B1 | 4/2001 | Ponzi |
| 6,284,971 | B1 | 9/2001 | Atalar et al. |
| 6,346,099 | B1 | 2/2002 | Altman |
| 6,628,980 | B2 | 9/2003 | Atalar et al. |
| 6,687,530 | B2 | 2/2004 | Dumoulin |
| 6,904,307 | B2 * | 6/2005 | Karmarkar et al. ...... 600/423 |
| 2001/0056232 | A1 * | 12/2001 | Lardo et al. ........... 600/423 |
| 2003/0023160 | A1 * | 1/2003 | Minkoff et al. ......... 600/423 |
| 2003/0028094 | A1 * | 2/2003 | Kumar et al. .......... 600/410 |
| 2004/0046557 | A1 | 3/2004 | Karmarkar et al. |

* cited by examiner

*Primary Examiner*—Brian Casler
*Assistant Examiner*—Peter Luong
(74) *Attorney, Agent, or Firm*—McKenna Long & Aldridge LLP

(57) ABSTRACT

A deflectable tip catheter that is safe and effective for use in a magnetic resonance imaging environment. The deflectable tip catheter is configured such that it includes a built-in antenna, such as a loopless antenna or a loop antenna. The built-in antenna permits the deflectable tip catheter to be actively tracked and/or visualized. Depending upon the specific configuration of the deflectable tip catheter, the catheter may be tracked and/or visualized as a single unit, it may be tracked and/or visualized separate and independent of other components or instruments associated with the catheter, such as pull wires, injection needles, surgical instruments, and the like. The catheters described herein include injection type catheters and/or guidance type catheters.

22 Claims, 22 Drawing Sheets

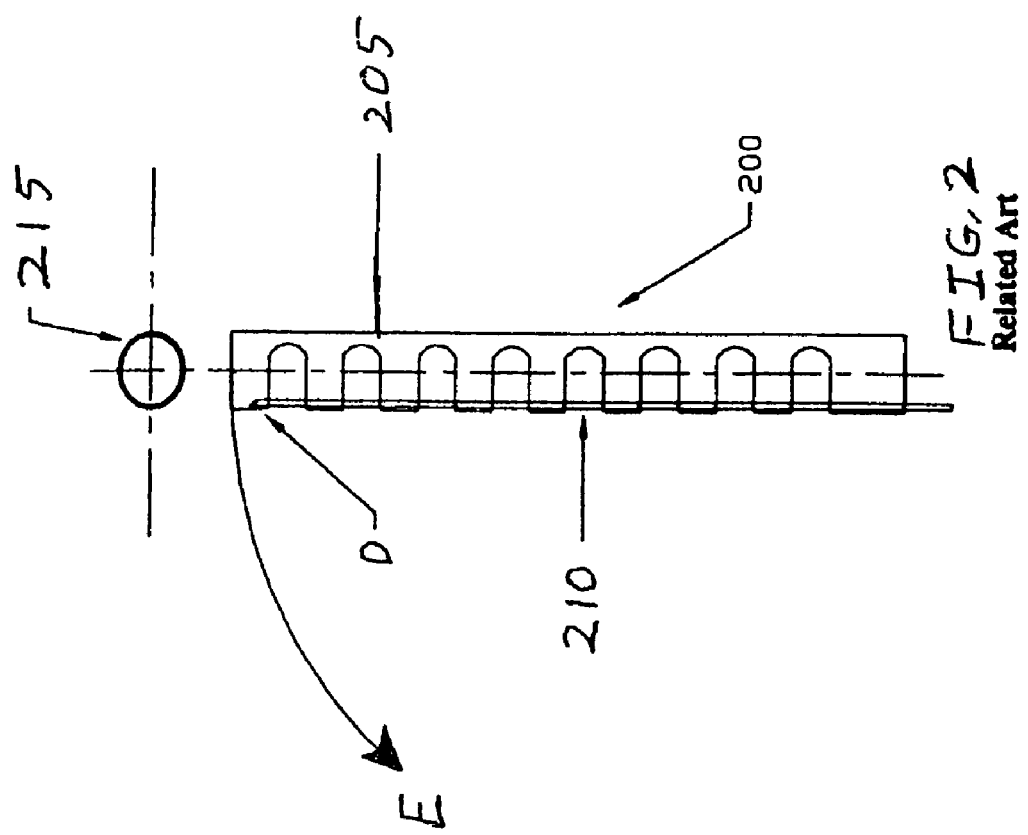

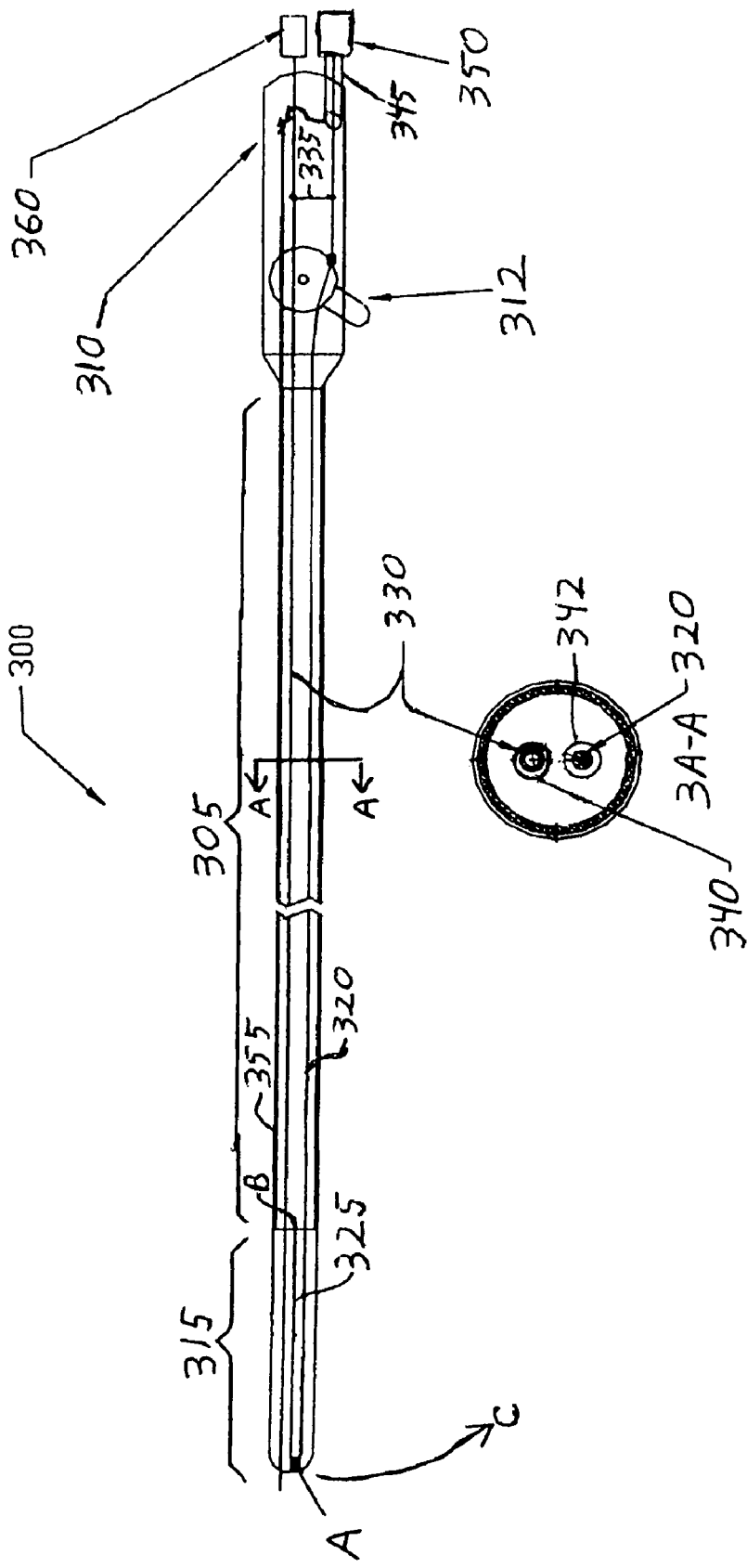

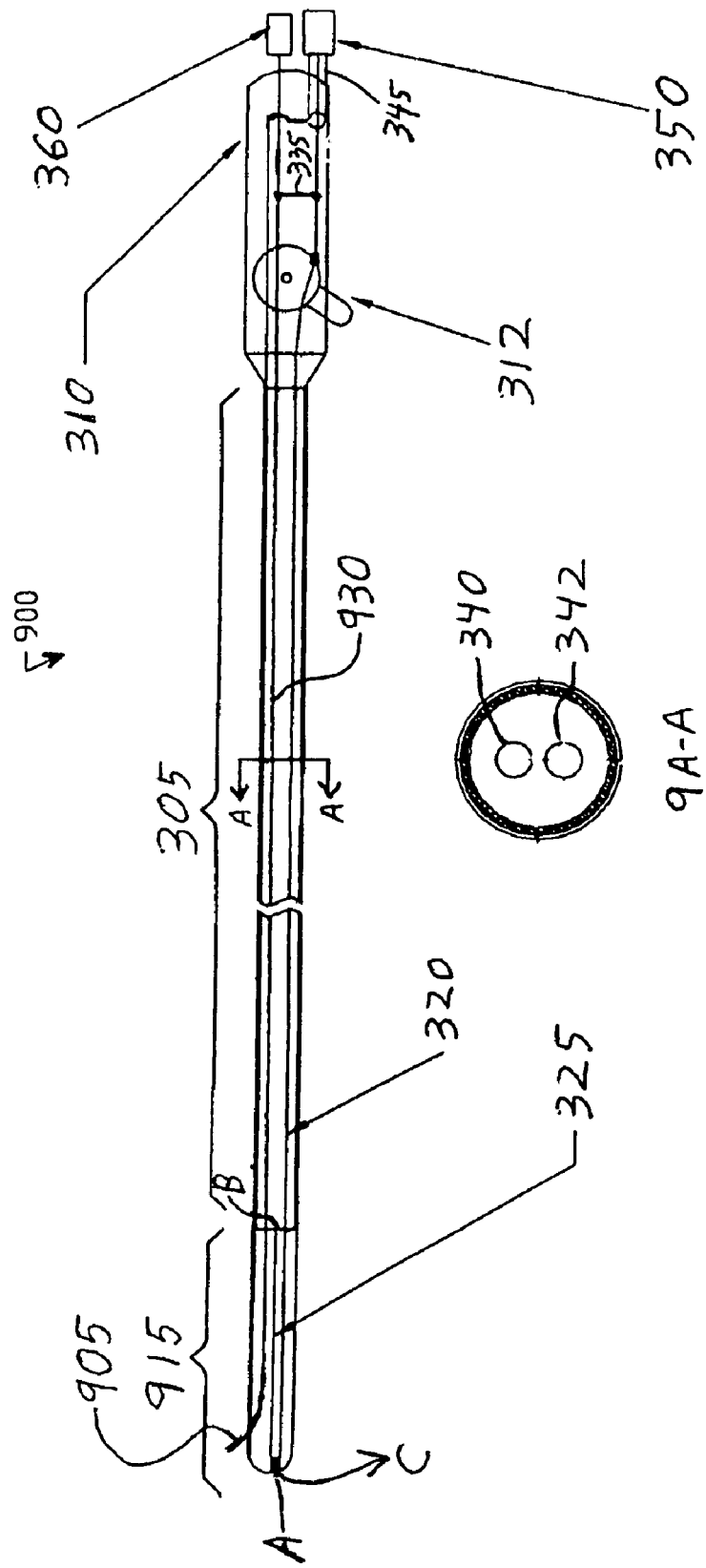

ACTIVE MRI INTRAMYOCARDIAL INJECITON CATHETER WITH A DEFLECTABLE DISTAL SECTION

The present application claims priority to U.S. Provisional Patent Application Ser. No. 60/444,430, filed Feb. 3, 2003, which is incorporated herein by reference, in its entirety.

BACKGROUND OF THE INVENTION

1. Field of the Invention

The present invention relates to catheters that have a deflectable portion. More particularly, the present invention relates to deflectable tip catheters that can be actively visualized and/or tracked in a magnetic resonance imaging (MRI) environment.

2. Discussion of the Related Art

Occlusive coronary artery disease results in myocardial infarction and deleterious left ventricular remodeling. Occlusive coronary artery disease can be treated. Treatment includes coronary balloon angioplasty, coronary artery stenting, and bypass graft surgery. However, due to the limited regenerative capacity of adult cardiomyocytes, ischemic events often result in irreversible cell injury and concurrent myocardial dysfunction, leading to congestive heart failure and death.

There is scientific evidence that delivering therapeutic agents, such as cells (e.g., stem cells), various genetic materials, growth factors, and the like, directly into the infarcted myocardial tissue may help to restore healthy tissue and normal myocardial function. Conventional interventional cardiology procedures, including the aforementioned treatments, such as balloon angioplasty, typically involve the use of a balloon catheter to dilate the occluded artery and X-ray fluoroscopy to assist the attending cardiologist guide the catheter. X-ray fluoroscopy, however, does not distinguish healthy from infarcted myocardial tissue, nor does it provide an anatomical image of the heart, where the ability to distinguish infarcted tissue from healthy tissue within an anatomical image of the heart is of vital importance to the cardiologist who is attempting to precisely deliver therapeutic agents using any one of the above-identified conventional techniques.

There are electro-anatomical mapping systems capable of providing a functional map of the cardiac anatomy; however, these systems cannot provide real-time images of the heart. An example is Biosense Webster's NOGA system, which is used in conjunction with X-ray fluoroscopy. The NOGA system employs a catheter comprising three coils and an endocardial potential measuring electrode located at the distal tip. During clinical use, three external magnets are placed at three different locations on the patient (e.g., under the patient's back and on the right and left side of the patient's chest). The cardiologist is then able to move the catheter around inside the left ventricle of the patient's heart, and, in doing so, the NOGA system measures the electrical activity at endocardial surface, as well as the motion and the location of the distal tip of the catheter. The NOGA system uses these measurements to create a three-dimensional, real-time, dynamic reconstruction of the ventricle, and assess the electrical and mechanical properties of the myocardium. The electrical potential and the motion of the ventricular wall are used, in turn, to differentiate between healthy, viable, tissue, and completely infarcted tissue. The primary drawback of this system is that it does not provide an anatomical image of the entire heart. It is therefore difficult to know the cardiac anatomy in which the catheter tip is located, and whether the catheter tip is opposed to the septum or the lateral wall. In addition, the procedure associated with the NOGA system is lengthy and the quality of the ventricle image is highly dependent on operator skill.

MRI is a diagnostic and imaging modality that is capable of providing a three-dimensional map, or image of the entire heart. Furthermore, MRI offers this capability without the ionizing radiation associated with other imaging modalities, such as X-ray fluoroscopy. MRI also provides real-time images with excellent tissue contrast; thus, the attending cardiologist can quickly and efficiently see the entire heart and clearly differentiate between healthy, viable, tissue and completely infarcted tissue. Ideally, MRI should be available to cardiologists for use during intervention therapy to accurately track and precisely guide the catheter to regions of infarcted myocardial tissue.

There are many types of injection catheters currently available; however, none is well suited for use in an MRI environment. For example, deflectable (i.e., steerable) tip catheters including multi-directional, bi-directional and uni-directional deflectable catheters are described in U.S. Pat. Nos. 5,487,757; 6,198,974; and 5,755,760, respectively. Injection catheters capable of delivering therapeutic agents to myocardial and other tissues are described, for example, in U.S. Pat. Nos. 5,980,516 and 6,004,295. Still further, deflectable injection type catheters are described, for example, in U.S. Pat. Nos. 6,346,099 and 6,210,362.

The various catheter designs described in the above-identified patents are not, as stated, well suited for use in an MRI environment for both procedural reasons as well as patient safety reasons. For instance, these catheters have ferromagnetic components that pose a safety hazard to the patient in a magnetic field environment, as they can cause injury to the patient, as they may move in an undesired manner due to the magnetic field. The ferromagnetic components can also cause image distortions, thereby compromising the effectiveness of the procedure. Still further, such catheters contain long metallic components, which can cause radiofrequency (RF) deposition in adjacent tissue and, in turn, tissue damage due to an extensive increase in temperature.

In addition, it would be difficult to track and/or visualize the location of the catheters described in the above-identified patents in an MRI environment. In general, there are two types of tracking in an MRI environment: active tracking and passive tracking. Active tracking is the preferred methodology. It involves incorporating a transmit and/or receive antenna into the catheter design. Because a high intensity signal is transmitted or received, active tracking provides precise location information. An example of a catheter that can be actively tracked in an MRI environment is described in U.S. Pat. No. 5,928,145. In this patent, the catheter employs a loopless antenna. Another example of a catheter that can be actively tracked in an MRI environment is described in U.S. Pat. No. 5,699,801. In this patent, the catheter does not have a deflectable tip, nor is it capable of delivering therapeutic agents to a target location, nor is it capable of deploying other surgical instruments such as forceps during a biopsy procedure.

It would be very desirable to provide attending cardiologists with a catheter design that he or she can easily steer. In addition, it would be desirable provide a catheter that can be effectively tracked and/or visualized in an MRI environment, a catheter that is safe and effective when used in an MRI environment, a catheter that can be used to effectively deliver therapeutic agents to a target location within the patient using an injection needle, and deploy other surgical instruments such as a laser, a suturing device, forceps, a cauterization tool, and the like.

SUMMARY OF THE INVENTION

Accordingly, the present invention is directed to a deflectable tip catheter that substantially obviates the deficiencies and disadvantages associated with the related art as set forth above. More specifically, the present invention is directed to a deflectable tip catheter that can be actively tracked in an MRI environment, without excessive RF deposition (i.e., local tissue heating) and the other safety and procedural drawbacks associated with the prior related art. The present invention is also directed to a deflectable tip catheter that can be effectively used to deliver therapeutics with an injection needle and deploy other surgical instruments during procedures, such as a biopsy procedure.

It should be noted that the following detailed description portrays the various exemplary embodiments of the present invention as being particularly useful in the field of cardiology. For example, the present invention is portrayed as being particularly useful for injecting and/or delivering therapeutics to cardiac tissue. However, it will be very clear to one skilled in the art that the present invention will be equally useful for other medical procedures, including biopsy procedures, as well as procedures that involve other anatomical systems such as the brain, liver, and pancreas.

As such, one advantage of the present invention is to provide a deflectable tip catheter that can be easily and effectively visualized and tracked in an MRI environment.

Another advantage of the present invention is to provide a deflectable tip catheter that can be employed safely when used in an MRI environment.

Still another advantage of the present invention is to provide a deflectable tip catheter that is effective when used in an MRI environment and does not, among other things, distort the image, and does not cause local tissue damage due to excessive RF deposition along the length of the catheter.

Thus, in accordance with exemplary embodiments of the present invention, the aforementioned and other objectives are achieved with a deflectable tip catheter for use in an MRI environment. The deflectable tip catheter comprises a deflectable tip section and an RF antenna.

In accordance with exemplary embodiments of the present invention, the aforementioned and other objectives are also achieved with a bi-directional, deflectable tip guide catheter. The bi-directional, deflectable tip guide catheter includes a deflectable tip section, a first pull wire, and a second pull wire, where the first and second pull wires are configured to form a loop antenna.

In accordance with exemplary embodiments of the present invention, the aforementioned and other objectives are further achieved with a deflectable tip catheter that includes a deflectable tip section and an RF antenna. In addition, the catheter includes a plurality of distally located, non-magnetic, inductor loop coils.

In accordance with exemplary embodiments of the present invention, the aforementioned and other objectives are still further achieved with a MRI system. The MRI system comprises an MRI scanner, a deflectable tip catheter that is configured as an RF antenna, and an electrical connection between the deflectable tip catheter and the MRI scanner.

In accordance with exemplary embodiments of the present invention, the aforementioned and other objectives are also achieved through a magnetic resonance imaging method. The method involves generating a magnetic field around at least a portion of a patient and transmitting RF energy over a portion of the patient exposed to the magnetic field. In addition, the method involves receiving the RF energy using an RF antenna in a deflectable tip catheter located in the patient and generating a magnetic resonance image that includes a visualization of the deflectable tip catheter in the patient.

BRIEF DESCRIPTION OF THE DRAWINGS

The accompanying drawings, together with the detailed description below, set forth the various aspects and embodiment of the present invention, wherein:

FIG. 2 is a schematic diagram of an alternative deflectable tip section 200 associated with a conventional deflectable tip catheter;

FIG. 3 is a schematic diagram of an active MRI trackable, deflectable tip injection catheter, in accordance with a first exemplary embodiment of the present invention;

FIGS. 9A and 9B are schematic diagrams of MRI trackable, deflectable tip injection catheters that include a side or lateral opening in the deflectable tip section, in accordance with a fourth exemplary embodiment of the present invention;

DETAILED DESCRIPTION OF THE ILLUSTRATED EMBODIMENTS

Figure 1:
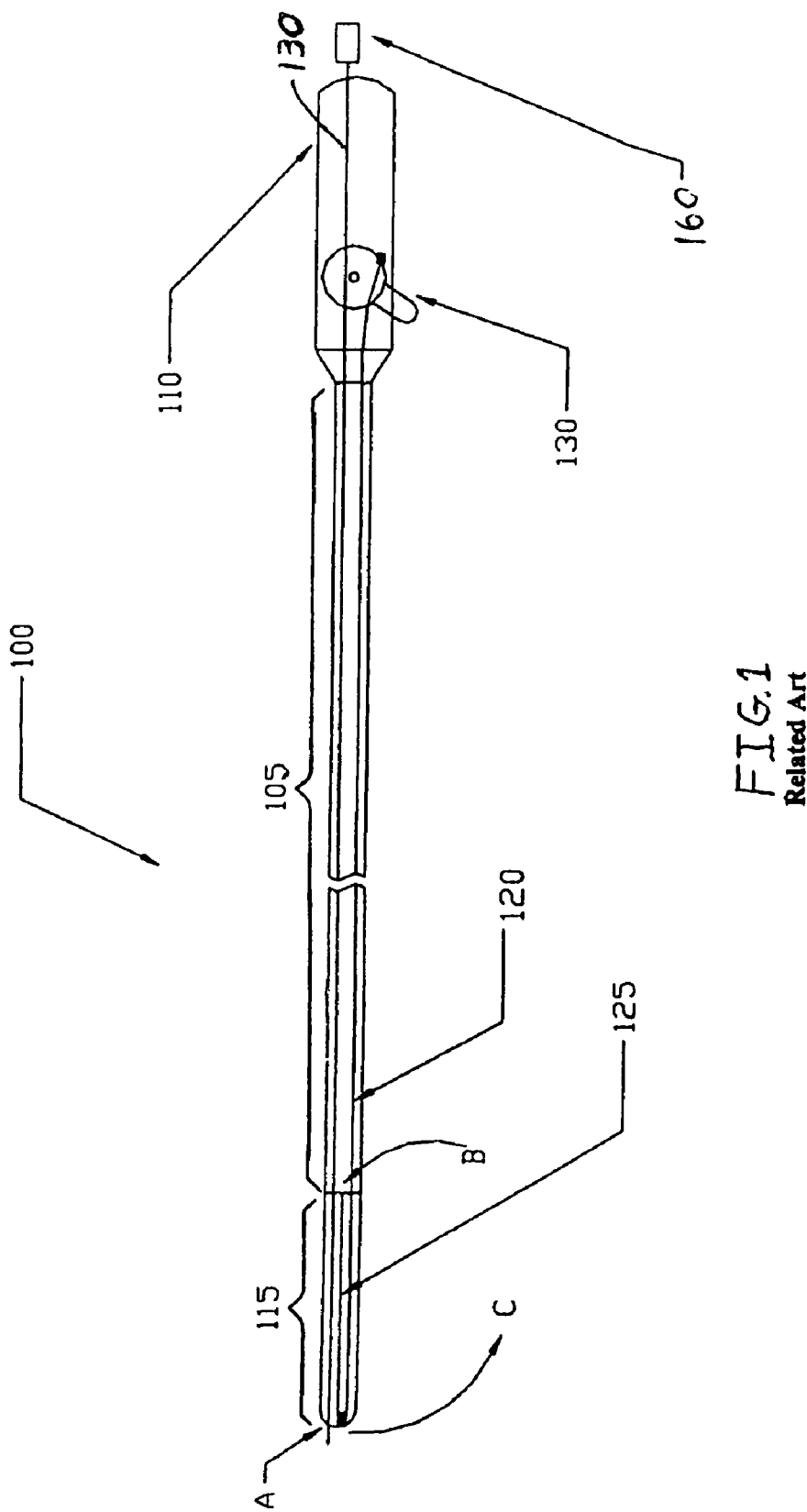
FIG. 1 is a schematic diagram of a conventional, deflectable tip injection catheter 100.

FIG. 1 is a schematic diagram of a conventional injection catheter 100 with a deflectable tip. As shown, the catheter 100 comprises a proximal portion that includes a non-deflectable section 105 and a handle 110. The catheter 100 also comprises a deflectable tip section 115. The deflection mechanism involves a pull wire 120 and an anchor wire 125, where the pull wire 120 and the anchor wire 125 are connected to each other at point A in the deflectable tip section 115, as shown. The pull wire 120 runs the length of the catheter through a lumen (not shown). The anchor wire 125 is fixed at point B where the distal end of the non-deflectable section 105 abuts the proximal end of the deflectable tip section 115. During clinical use, the attending physician (e.g., cardiologist) may actuate the deflectable tip section 115 by manipulating the deflection dial 130 on the handle 110. This action causes the pull wire 120 to move in the direction of the handle, relative to the anchor wire 125. As the anchor wire 125 is fixed, the movement of the pull wire 120 causes the deflectable tip section 115 to deflect as shown, for example, by arrow C. One skilled in the art will readily appreciate the fact that an injection needle 133, having a luer 160 at a proximal end, may run the length of the catheter 100, parallel or essentially parallel to the pull wire 120, through a second lumen (not shown), where the needle 130 is typically made of metal, polymer, or a combination of both. Again, the drawbacks associated with catheters, such as catheter 100, when employed in an MRI environment include image distortion, burns due to RF heat deposition, the inability to accurately track the position and/or location of the catheter 100 during MRI scanning.

FIG. 2 is a schematic diagram of an alternative deflectable tip section 200 associated with a conventional deflectable catheter. As shown, the deflectable tip section 200 comprises a slotted, metallic hypotube 205. Examples of catheters comprising a slotted deflectable tip section can be found in U.S. Pat. Nos. 4,898,577 and 5,030,204. In FIG. 2, a pull wire 210 is connected to the distal end of the slotted tube at point D, as shown. Moving the pull wire 210 in a proximal direction causes the deflectable tip section 200 to deflect as indicated by arrow E. Again, it will be understood by one of ordinary skill in the art that the corresponding catheter may be used as a delivery device to advance a tool such as an injection needle (not shown) through lumen 215 of the catheter 200 to carry out an injection and is described, for example in U.S. Pat. No. 6,102,887.

FIG. 3 is a schematic diagram of an active MRI tracking, injection catheter 300, with a deflectable tip, in accordance with a first exemplary embodiment of the present invention. More particularly, the catheter 300 is a single or uni-direction, deflectable tip MRI active injection catheter arranged as a loopless antenna with multiple cores. The catheter 300 has a proximal portion that includes a non-deflectable section 305 and a handle 310, as well as a needle 330, having a luer 360 at a proximal end. The catheter 300 also has a distal, deflectable tip section 315. In addition, catheter 300 includes a pull wire 320 and an anchor wire 325, where the pull wire 320 is run through a polymeric tube 342, as shown, and where the anchor wire 325 is connected to the pull wire 320 at point A and is fixed at point B. In this exemplary embodiment, the anchor wire 325 is a flat wire, which limits the deflection of deflectable tip section 315 to the direction indicated by arrow C. However, it will be readily understood that the anchor wire 325 may be other than a flat wire, thereby allowing for deflection in more than the one direction indicated by arrow C. Together, the pull wire 320 and the anchor wire 325 make up a first core. It should be noted that the anchor wire 325 can be made of an elastic material and it may be oval, elliptical, flat, triangular, and the like, in its cross-section. The pull wire 320 too may take on other shapes in cross-section.

The catheter 300 includes a second core. In the exemplary embodiment illustrated in FIG. 3, the second core is a needle 330, which may be employed to deliver therapeutic agents, as set forth above. The needle 330, having a luer 360 at a proximal end, runs through a needle tube 340. In a preferred embodiment, the needle 330 and the pull wire 320 run through separate tubes 340 and 342, respectively. Alternatively, the needle 330 and the pull wire 320 may run through a single tube in the distal, deflectable tip section 315. In another alternative to the first exemplary embodiment, an instrument other than or in addition to the needle 330 may be used, such as surgical forceps, where an additional instrument would preferably run through a separate corresponding tube, parallel or essentially parallel to the needle tube 340 and the polymeric tube 342.

The overall length of the catheter 300 might range from approximately 10 cm to approximately 200 cm, where the length of the distal, deflectable tip section 315 may range in length from 0.5 cm to 30 cm, though a length between 1 cm and 6 cm is more common. The proximal, non-deflectable portion 305 might have a length of approximately 10 cm to 199 cm. These lengths are intended to be illustrative and not limiting in any way as to the present invention. As one of skill in the art will appreciate, the length of any catheter in accordance with the various embodiments of the present invention can and will vary depending on the intended use and application for which the catheter is being employed.

As shown in FIG. 3, the needle 330 and the pull wire 320 are electrically connected, for example, at electrical connection 335 in the handle 310, where the pull wire 320 and the needle 330 together serve as the cores of a loopless catheter antenna. The loopless catheter antenna is connected to an interface/decoupling circuit, also referred to as a matching-tuning circuit, such as the circuits illustrated in FIG. 5A or 5B, via a coaxial cable 345 and BNC (e.g., a micro BNC) connector 350. The matching-tuning circuit tunes the antenna to the appropriate frequency so the catheter 300 may be actively tracked within an MRI environment. The catheter antenna and the matching-tuning circuit are connected to the MRI scanner by a coaxial cable. The matching-tuning circuits in FIGS. 5A and 5B will be described in greater detail below.

The non-deflectable portion 305 of catheter 300 is covered by a braided tube 355, which acts as an RF shield for the loopless antenna. The braiding is preferably made from MRI compatible material, such as nitinol, tungsten, MP35N, copper, or other like materials. Alternatively, the non-deflectable portion 305 may be covered by a shield made from flexible MRI compatible hypotubing, where the hypotubing may be laser cut at different locations along its length, or heat-treated to modify the mechanical properties, so as to make the tubing flexible.

As stated, the proximal end of the catheter 300 includes a handle 310. The handle 310 houses, among other features, a deflection dial 312. The deflection dial 312 is part of the deflection mechanism. Manipulation of the deflection dial 312 causes the pull wire 320 to move relative to the anchor wire 325 which, in turn, causes the distal, deflectable tip section 315 to deflect under the constraint of anchor wire 325, for example, in the direction indicated by arrow C. The matching-tuning circuits 500 and 501 illustrated in FIGS. 5A and 5B may be located in the handle of the deflectable tip catheter 300, in which case, the handle of the catheter will be directly connected to the MRI scanner via a coaxial cable.

Figure 4A:
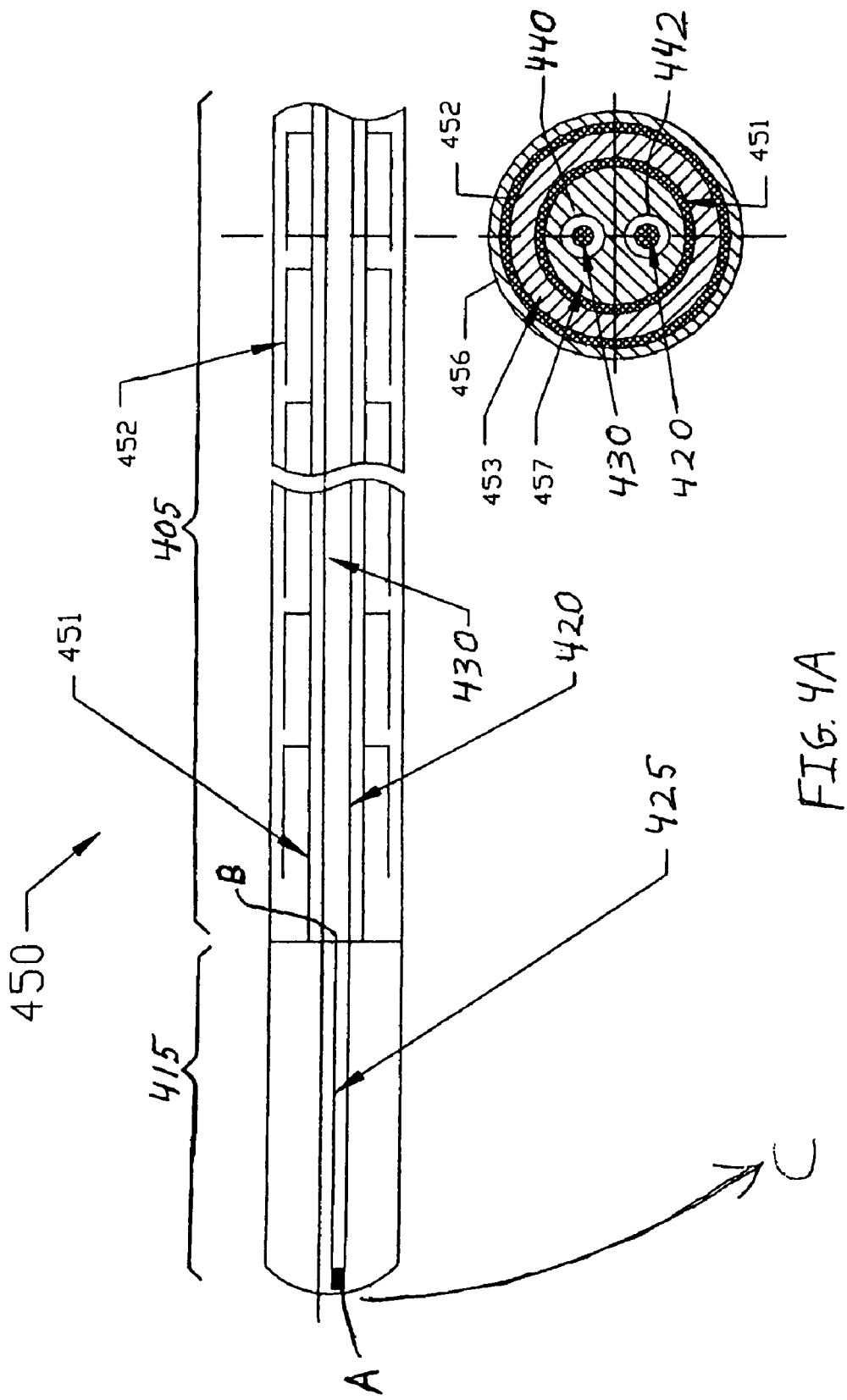
FIG. 4A is a schematic diagram of a catheter having a non-deflectable portion that includes multiple RF chokes, in accordance with an alternative embodiment.

FIG. 4A is a schematic diagram of a catheter 450 having a non-deflectable portion 405 that includes the added safety feature of multiple RF chokes 452, in accordance with an alternative to the first exemplary embodiment illustrated in FIG. 3. This alternative embodiment may be particular useful in the event the non-deflectable portion 405 of the catheter is excessively long, and there is added concern over heat buildup along this portion of the catheter 450. As shown in FIG. 4A, the non-deflectable portion 405 has primary shielding 451 and secondary shielding 452, where the secondary shielding 452 has a length that is less than one-quarter wavelength (λ/4) and is connected to the primary shielding 451 at one end. At the other end, there may be a capacitor (not shown) located between the primary shielding 451 and the secondary shielding 452, or simply a stray capacitance resulting from the close proximity of the primary and secondary shielding, where there is a primary insulation layer 453 between the primary shielding 451 and the secondary shielding 452. In addition, the secondary shielding 452 is, as shown, discontinuous. There is also a secondary insulation layer 456, located radially outside the secondary shielding 452. In a preferred embodiment, there is dual lumen tubing 457 running the length of the catheter 450, where a first lumen 442 is for pull wire 420, and the other lumen 440 is for a surgical instrument, such as a needle 430.

It will be apparent that the needle 430 can extend beyond the distal deflectable tip 415, for example, in order to deliver or inject a therapeutic agent (e.g., cells, drugs, genetic material, other biological materials, and the like) into tissue during a clinical procedure. The mechanism for manipulating the needle 430 may include a spring mechanism (not shown) for injecting the needle 430 into tissue. The spring mechanism may be located in the distal, deflectable tip section 415 or in the handle (not shown, similar to 310). The mechanism for operating the needle 430 may also include a luer (not shown, similar to luer 360 which facilitates the attachment of a syringe (not shown) containing the therapeutic agent that is to be delivered to the tissue.

Figure 4B:
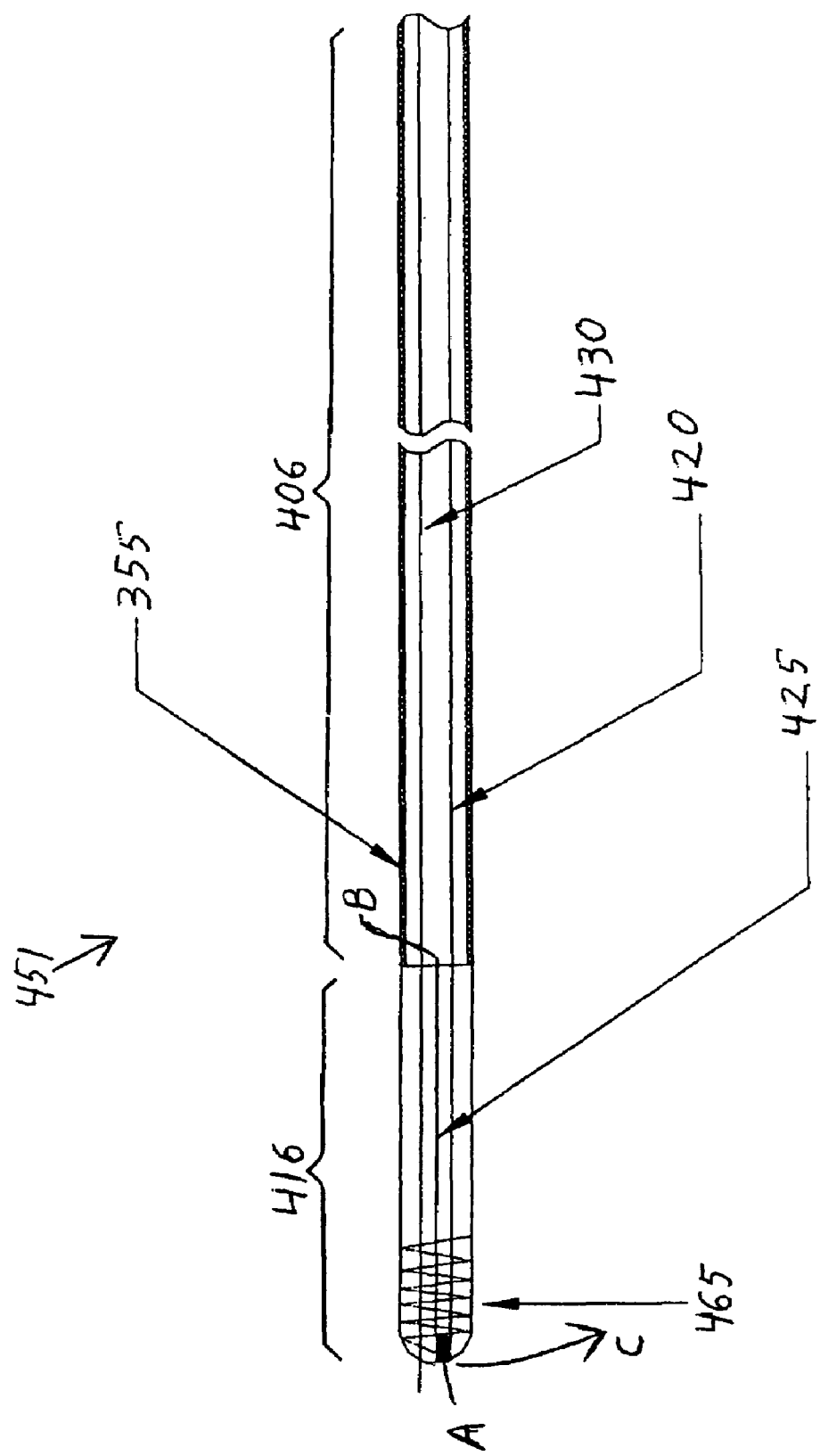
FIG. 4B is a schematic diagram illustrating an alternative deflectable tip section for an injection catheter in accordance with an alternative embodiment.

FIG. 4B is a schematic diagram illustrating an alternative distal, deflectable tip section 416 for the injection catheter 451 of FIG. 4B. As shown, the catheter 451 includes, in the distal, deflectable tip section 416, a pull wire 421 and an anchor wire 426. As was the case for the embodiment illustrated in FIG. 3, the anchor wire 426 is connected to the pull wire 421 at point A in the deflectable tip section 416 and fixed at a point B, where the proximal end of the deflectable tip section 416 meets the distal end of the non-deflectable portion 406. The catheter 451 also includes an MRI compatible (i.e., non-magnetic), insulated metallic wire 465 connected to the pull wire 420 or the needle 430, where the metallic wire 465 is coiled backwards upon itself, as shown. The coiled wire 465 increases the MRI signal intensity associated with the distal tip of the catheter 451. Thus, the deflectable tip 416 is more visible as compared to the rest of the catheter in the MRI image, making it easier for the attending physician to locate and track the catheter 451.

Figure 5A:
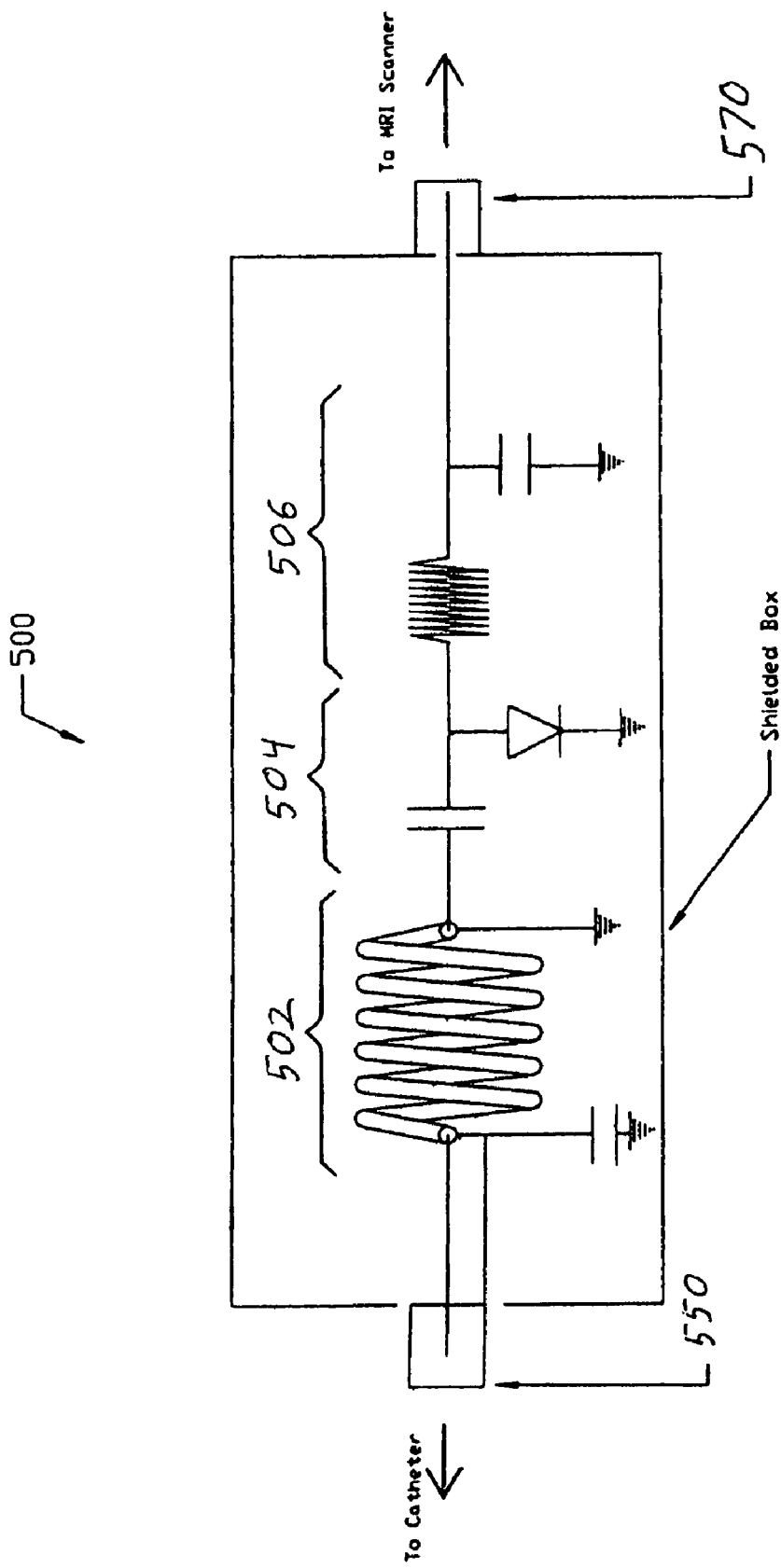
FIG. 5A is a circuit diagram of a single RF output signal matching-tuning circuit that may be employed with a deflectable tip injection catheter, in accordance with exemplary embodiments of the present invention.

FIG. 5A is a circuit diagram of a matching-tuning circuit 500 that may be employed if the needle 330 and the pull wire 320 are electrically connected or shorted at the proximal end in the handle section, as shown, for example, by electrical connection 335 in FIG. 3. In a preferred embodiment, matching-tuning circuit 500 includes a balun 502, which prevents shield currents induced on the connecting coaxial cable (i.e., between the matching-tuning circuit 500 and the MRI scanner) from being transmitted to the catheter 300; decoupling circuitry 504, which decouples/detunes the catheter when the MRI scanner is transmitting RF energy, thus preventing excessive RF deposition along the length of the catheter 300; and matching-tuning circuitry 506, which tunes the loopless antenna associated with catheter 300 to the operating frequency of the MRI scanner (not shown), for example, 64 MHz at 1.5 Tesla.

If the needle 330 and the pull wire 320 are electrically connected, such as by electrical connection 335, there is but one RF output signal associated with the loopless antenna, as shown by the single coaxial cable 345. Thus, the matching-tuning circuit 500 has but one electrical connection through the BNC connector 550, where the BNC connector 550, in FIG. 5A, connects with the BNC connector 350 in FIG. 3. The matching-tuning circuit 500 also has a BNC connector 570, which is electrically connected to the MRI scanner, via a coaxial cable (not shown). As there is but one RF output signal, the MRI scanner cannot separately and independently track the pull wire 320 (i.e., cannot separately and independently track the catheter, which serves as the first core of the loopless antenna) and the needle 330 (i.e., the second core of the loopless antenna).

Figure 5B:
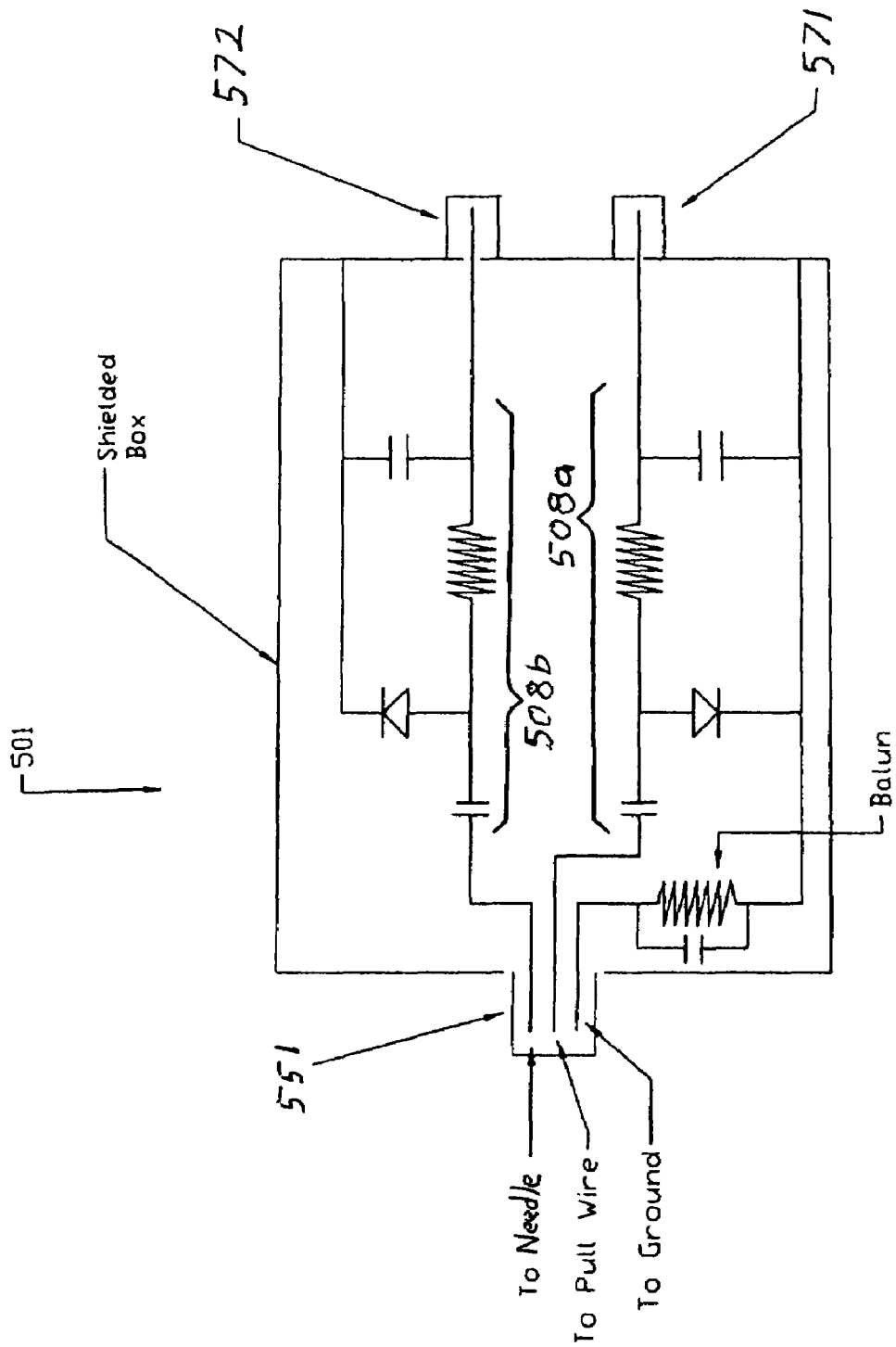
FIG. 5B is a circuit diagram of a multiple RF output signal matching-tuning circuit that may be employed with a deflectable tip injection catheter, in accordance with exemplary embodiments of the present invention.

FIG. 5B is a circuit diagram of a matching-tuning circuit 501 that may be employed if the needle 330 and the pull wire 320 are not electrically connected. As shown, matching-tuning circuit 501 has a decoupling and matching-tuning circuit 508a for the pull wire 320 and a separate decoupling and matching-tuning circuit 508b for the needle 330. In addition, the matching-tuning circuit 501 includes a BNC connector 551 with multiple insulated cores or a multi-pin connector, a BNC connector 571 and a BNC connector 572. BNC connector 551 contains three separate electrical conductors: one for the needle 330, one for the pull wire 320, and one that serves as a ground connection. BNC connector 571 is electrically connected to the MRI scanner via a coaxial cable (not shown), and the electrical conductor associated with the BNC connector 571 carries the output signal associated with the pull wire 320. Similarly, BNC connector 572 is electrically connected to the MRI scanner via a coaxial cable (not shown), and the electrical conductor associated with the BNC connector 572 carries the output signal associated with the needle 330. As there are two separate output signals, one for the needle 330 and one for the pull wire 320, the MRI scanner can separately and independently track the position and location of the needle 330 and the pull wire 320. As the pull wire 320 always remains inside the catheter 300, it will be understood that tracking the position and location of the pull wire 320 equates to tracking the position and location of the catheter 300.

Figure 6:
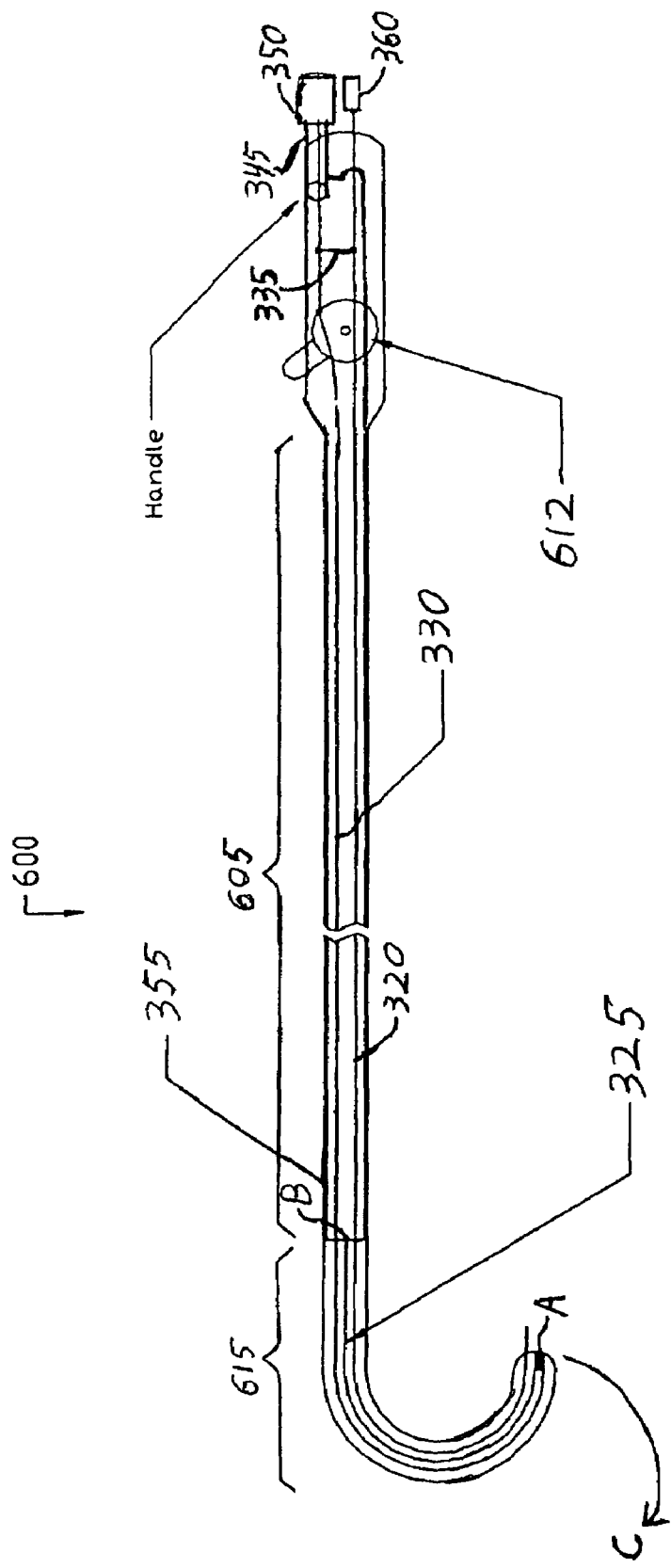
FIG. 6 is a schematic diagram of an MRI trackable, deflectable tip injection catheter that has a pre-deflected (i.e., pre-shaped), distal deflectable tip section, in accordance with a second exemplary embodiment of the present invention.

FIG. 6 is a schematic diagram of an injection catheter 600 in accordance with a second exemplary embodiment of the present invention. As shown in FIG. 6, the distal, deflectable tip section 615 is pre-shaped into a relatively small radius, so the catheter 600 can more easily traverse through, for example, the aortic valve without causing damage. The catheter 600 is typically advanced into the left ventricle through the femoral artery and across the aortic arch through the aortic valve. Once in the left ventricle, the attending physician can manipulate the deflection dial 612 to deflect the tip of the catheter 600. To facilitate the retraction of the catheter 600 from the left ventricle, the attending physician may straighten the distal, deflectable tip section 615, as indicated by arrow A, by manipulating the deflection dial 612 appropriately.

Figure 7:
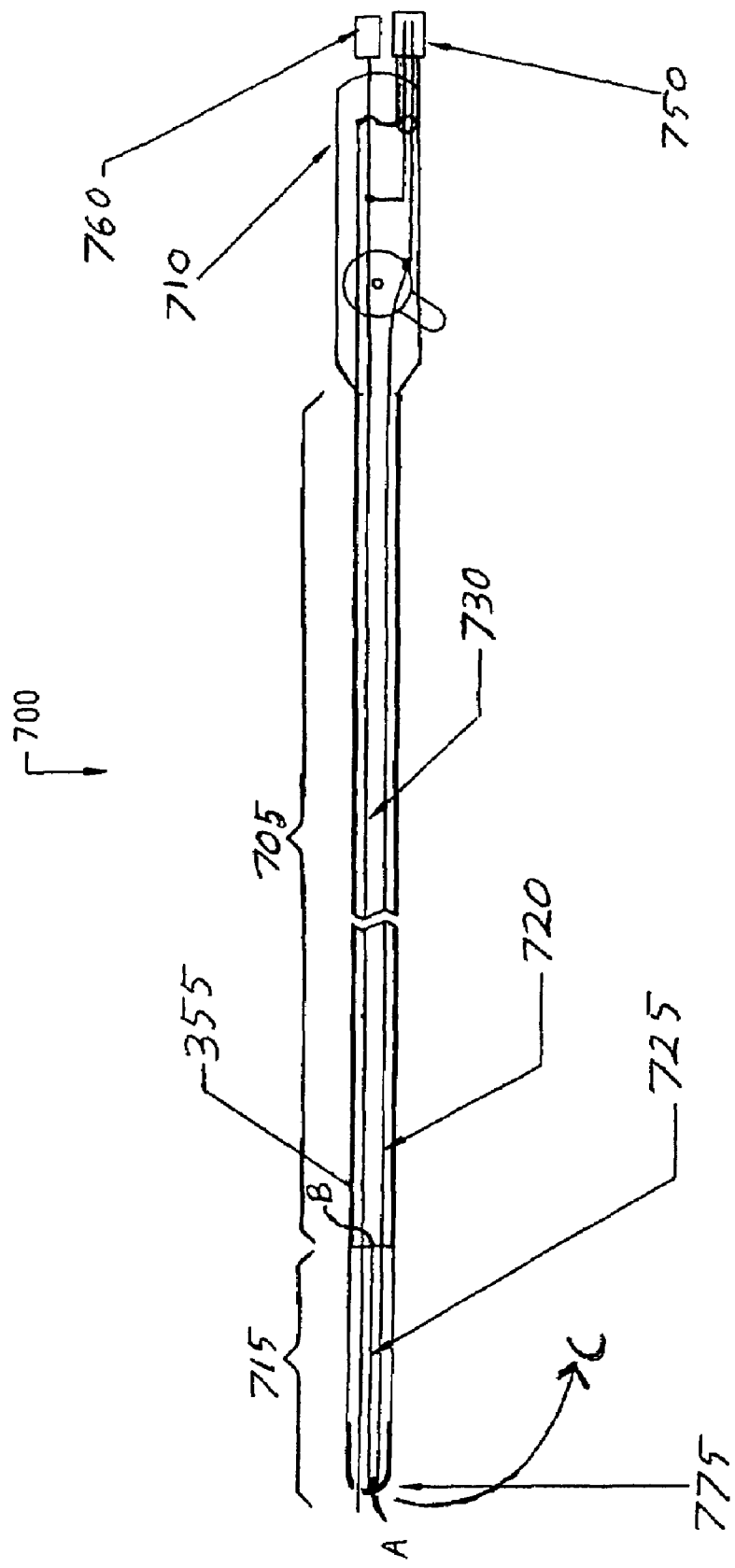
FIG. 7 is a schematic diagram of an MRI trackable, deflectable tip injection catheter that includes an endocardial potential measuring electrode, in accordance with a third exemplary embodiment of the present invention.

FIG. 7 is a schematic diagram of an injection catheter 700 in accordance with a third exemplary embodiment of the present invention. In this embodiment, the catheter 700 includes an electrode 775 built into the distal end of the deflectable tip section 715. This electrode 775 may be used to measure the electrical potential of adjacent tissue (e.g., endocardial tissue). Although the catheter 700, illustrated in FIG. 7, has but one electrode 775, it will be apparent to those skilled in the art that it would be feasible to employ more than a single electrode.

Figure 8:
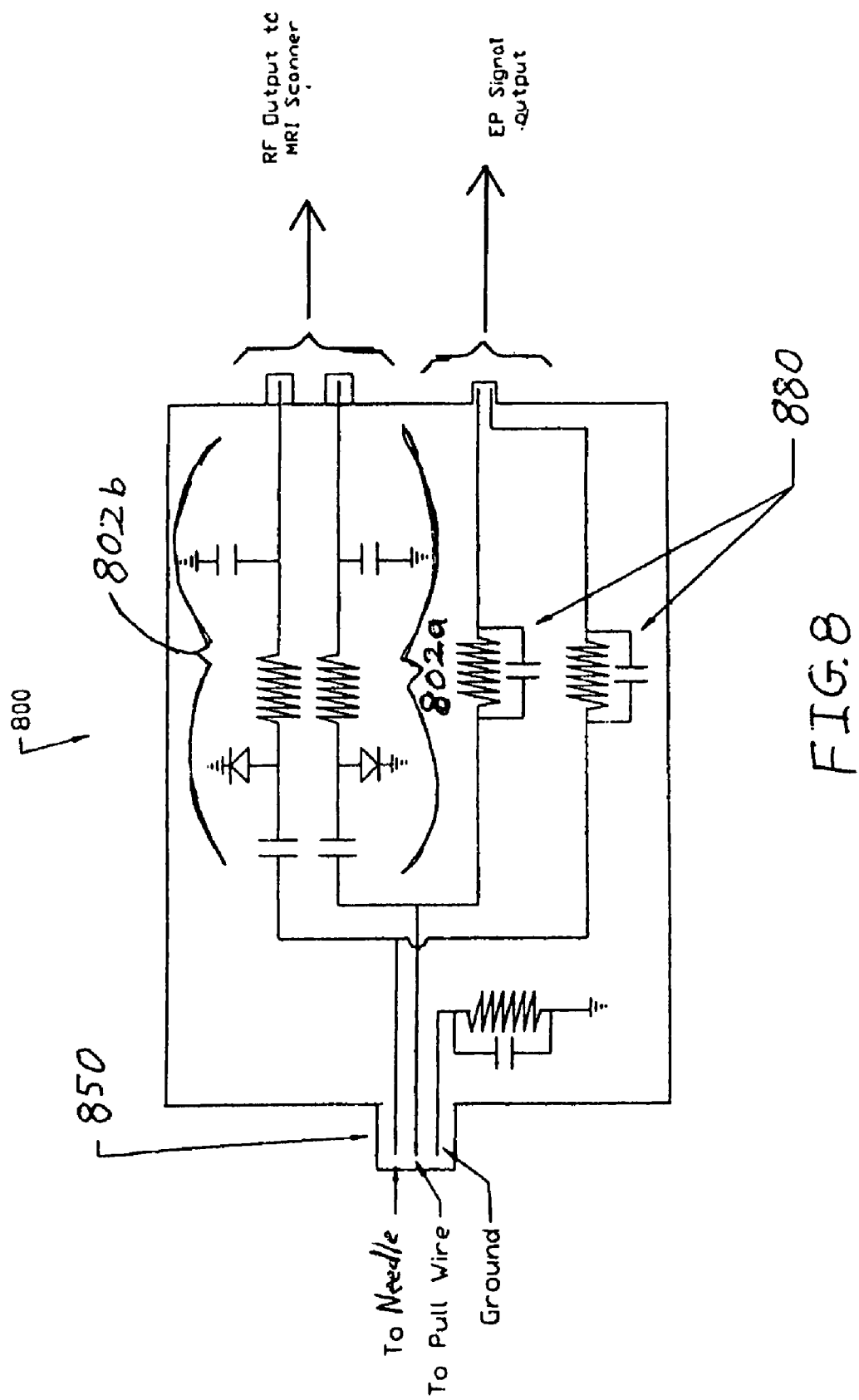
FIG. 8 is a circuit diagram of an interface circuit that may be used in conjunction with a deflectable tip injection catheter that has an endocardial potential measuring electrode.

FIG. 8 is a circuit diagram of an exemplary matching-tuning circuit 800 that may be used in conjunction with injection catheter 700 illustrated in FIG. 7. As shown, matching-tuning circuit 800, like matching-tuning circuit 501 in FIG. 5B, has separate RF input leads for the pull wire 720 and the needle 730. A multi-pin connector 750 may connect to a corresponding multi-pin connector 850 of the matching tuning circuit 800. In addition, there are separate decoupling and matching-tuning circuits 802a and 802b for the pull wire 720 and the needle 730, respectively. Accordingly, the MRI scanner will be able to separately track the position and location of the catheter 700 (i.e., by tracking the position and location of the pull wire 720) and the needle 730. The matching-tuning circuit 800 also includes RF blocking circuitry 880. The RF blocking circuitry 880 filters out any RF components associated with the MRI system so that those components are not coupled to the electrical potential output signal lines. Thus, the Electrical Potential signal output will more accurately reflect the electrical potential of the tissue adjacent to the distal end of the deflectable tip section 715 of catheter 700.

In the embodiments described above, the needle, as stated previously, is preferably made of MRI compatible metal, e.g., nitinol, MP35N, titanium, tantalum, gold, platinum, various non-ferromagnetic alloys, and the like. In addition, the needle may be selectively heat-treated; for example, the distal end of the needle may be heat treated, such as the last 10 cm of the needle. By heat-treating the distal end of the needle, the distal end of the needle can be adjusted for stiffness and made more flexible than the proximal portion of the needle. This makes it easier for the attending physician to advance the needle into adjacent tissue (e.g., myocardial tissue) particularly when the distal tip of the catheter is deflected. The needle may also be coated with a hydrophilic or hydrophobic coating on the inside and/or outside to enhance injection rates and reduce the shear stress experienced by cells being injected through the needle. Still further, the outer surface of the needle may be electroplated using a conducting metal, such as gold, silver, copper or the like, to enhance the RF and/or the electrical potential signal associated with the needle.

In the embodiments described above, the injection catheters employ but one needle. However, it will be evident that more than one needle may be employed, where each would serve as a separate core for the loopless antenna. The attending physician would, of course, have the ability to advance each needle individually, where each needle may contain a different therapeutic agent.

Figure 9B:
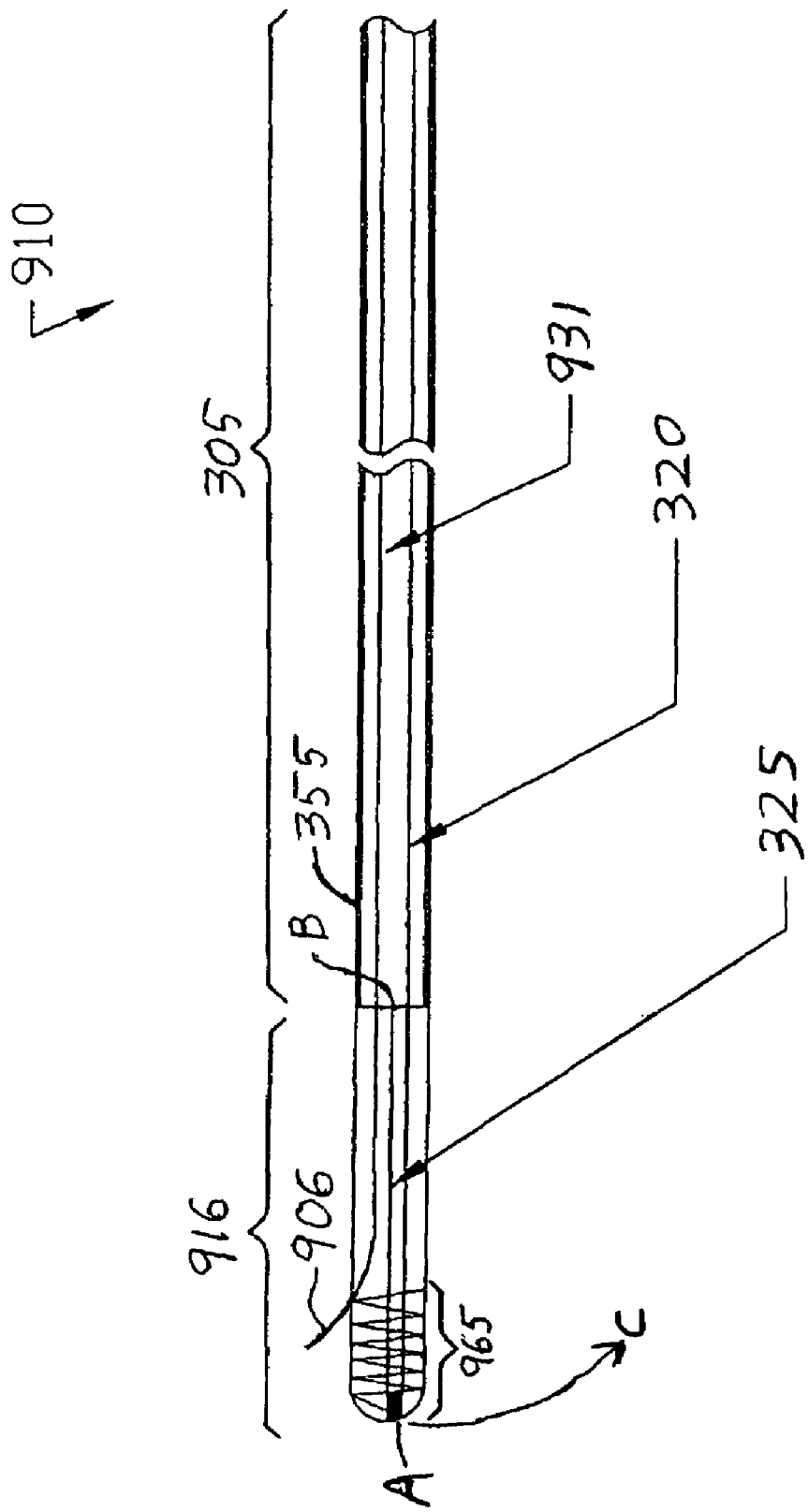

In each of the embodiments described above, the needle projects through the distal end of the deflectable tip section of the injection catheter. However, FIGS. 9A and 9B are schematic diagrams of an injection catheter 900 and an injection catheter 901, respectively, in accordance with a fourth exemplary embodiment of the present invention, wherein the injection needle 930, 931 project through a side or lateral opening 905, 906 in the deflectable tip section 915, 916 of the catheters 900, 901, respectively, rather than an opening in the distal end of the deflectable tip section of the catheter. But for the side or lateral needle openings 905, 906 injection catheters 900, 901 have the same, or substantially the same, configuration as injection catheter 300 and injection catheter 451, as illustrated in FIG. 3 and FIG. 4B, respectively. Alternatively, the injection catheter 900, 901 may contain one or more needles and have multiple needle outlets through which the attending physician may advance a needle, including an opening in the distal end of the deflectable tip section 915, 916, as well as one or more lateral openings. Similarly, needles may be concentrically placed one inside the other and advanced by the attending physician in a telescopic fashion.

Side or lateral needle openings may be quite beneficial during certain procedures. For example, a catheter as illustrated in FIG. 9A or 9B may be advanced into a coronary artery. The needle may then be advanced more easily through a side or lateral opening, in the deflectable tip section, through the arterial wall and into the adjacent myocardium to enable delivery of a therapeutic into the tissue. Such a catheter would also be useful in a vascular bypass procedure.

There are many additional features associated with the catheter needle that may be incorporated into the various embodiments of the present invention. For example, the catheter may have a mechanism, preferably located on or near the handle of the catheter, for locking the needle in place, releasing the needle from a locked position, and controlling the extent of needle insertion into adjacent tissue. For example, it may be useful to lock the needle in a retracted position to prevent the accidental injection of a therapeutic agent.

Figure 10A:
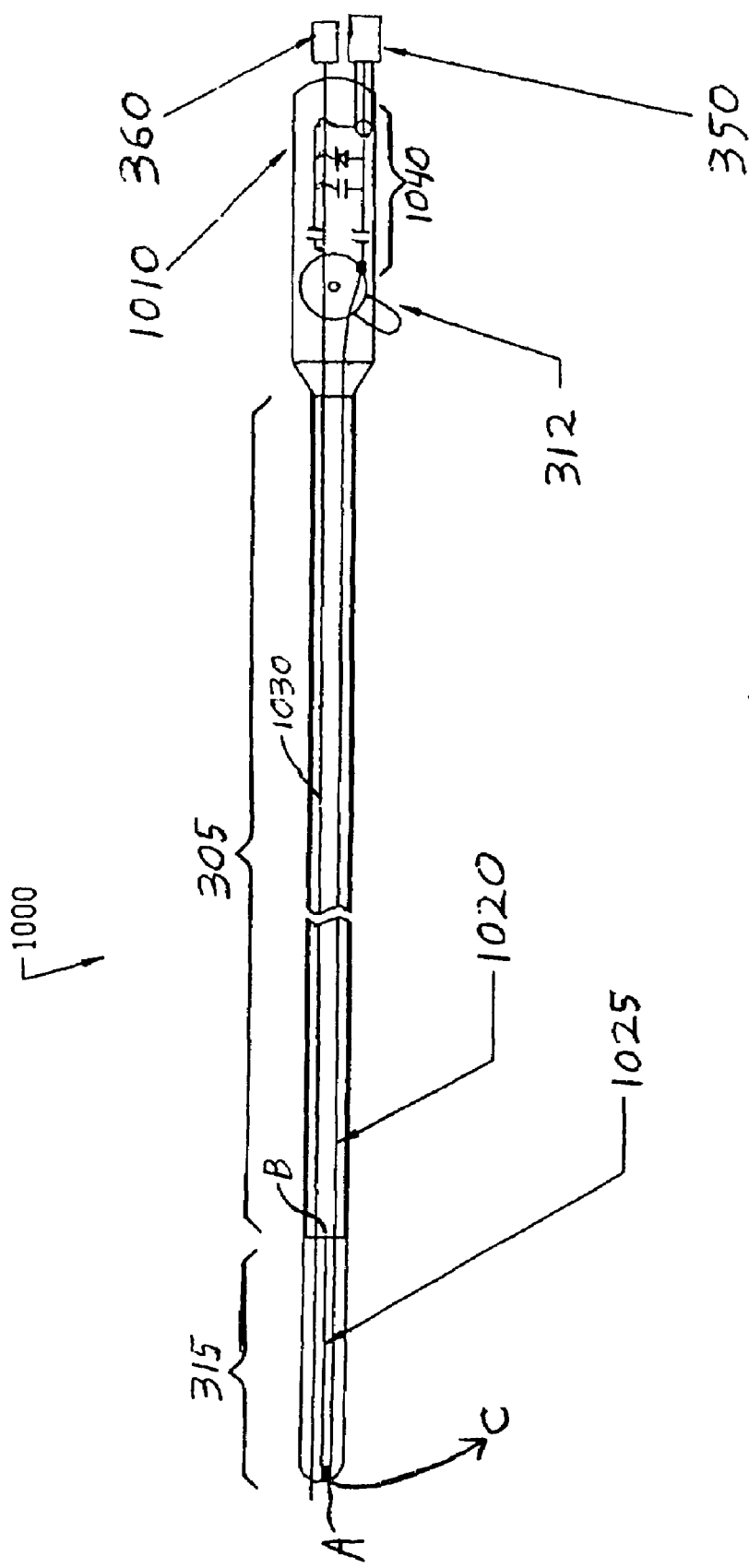
FIG. 10A is a schematic diagram of an MRI trackable, deflectable tip injection catheter, in accordance with a fifth exemplary embodiment of the present invention.

FIG. 10A is a schematic diagram of an injection catheter 1000, in accordance with a fifth exemplary embodiment of the present invention. In this embodiment, the needle 1030 and the pull wire 1020 serve as parallel wires of an elongated loop antenna, rather than a loopless antenna. The matching-tuning circuit 1040 for decoupling and tuning the loop antenna is shown as being located in the handle 1010 of the injection catheter 1000. However, the matching-tuning circuit could be externally located, like the previous embodiments described above.

Figure 10B:
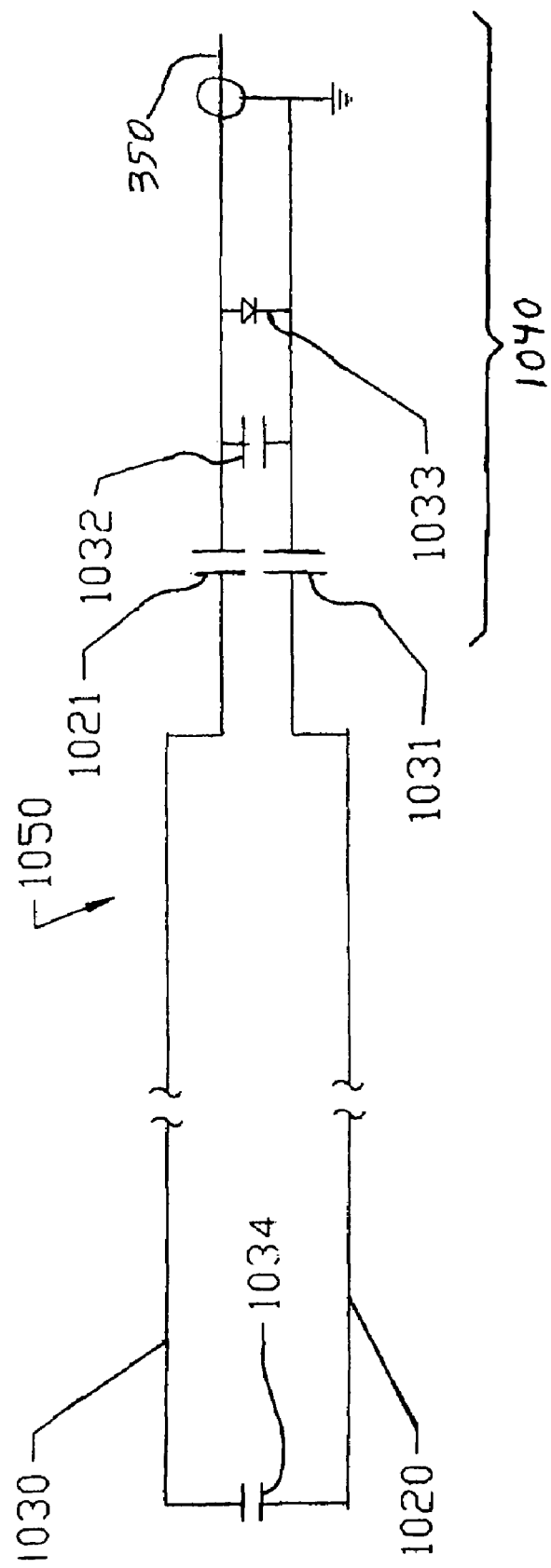
FIG. 10B is a schematic diagram of an interface circuit that might be used in conjunction with a deflectable tip injection catheter, in accordance with exemplary embodiments of the present invention.

FIG. 10B is a schematic diagram that more clearly depicts a matching-tuning circuit 1040 that might be used in conjunction with the injection catheter 1000. The circuit 1040 includes an electrical connector or lead 350 for the pull wire 1020 and the needle 1030, a series capacitor 1021, a series capacitor 1031, a parallel capacitor 1032, and a PIN diode 1033. There may also be a series capacitor 1034 at the distal end of the inductor loop, or there may be stray capacitance induced by the close proximity of the two conductors and the dielectric therebetween. The parallel capacitor 1032 and the PIN diode 1033 serve as the decoupling circuitry. It will be understood, however, that other matching-tuning circuit configurations may be employed with the catheter 1000.

Figure 11:
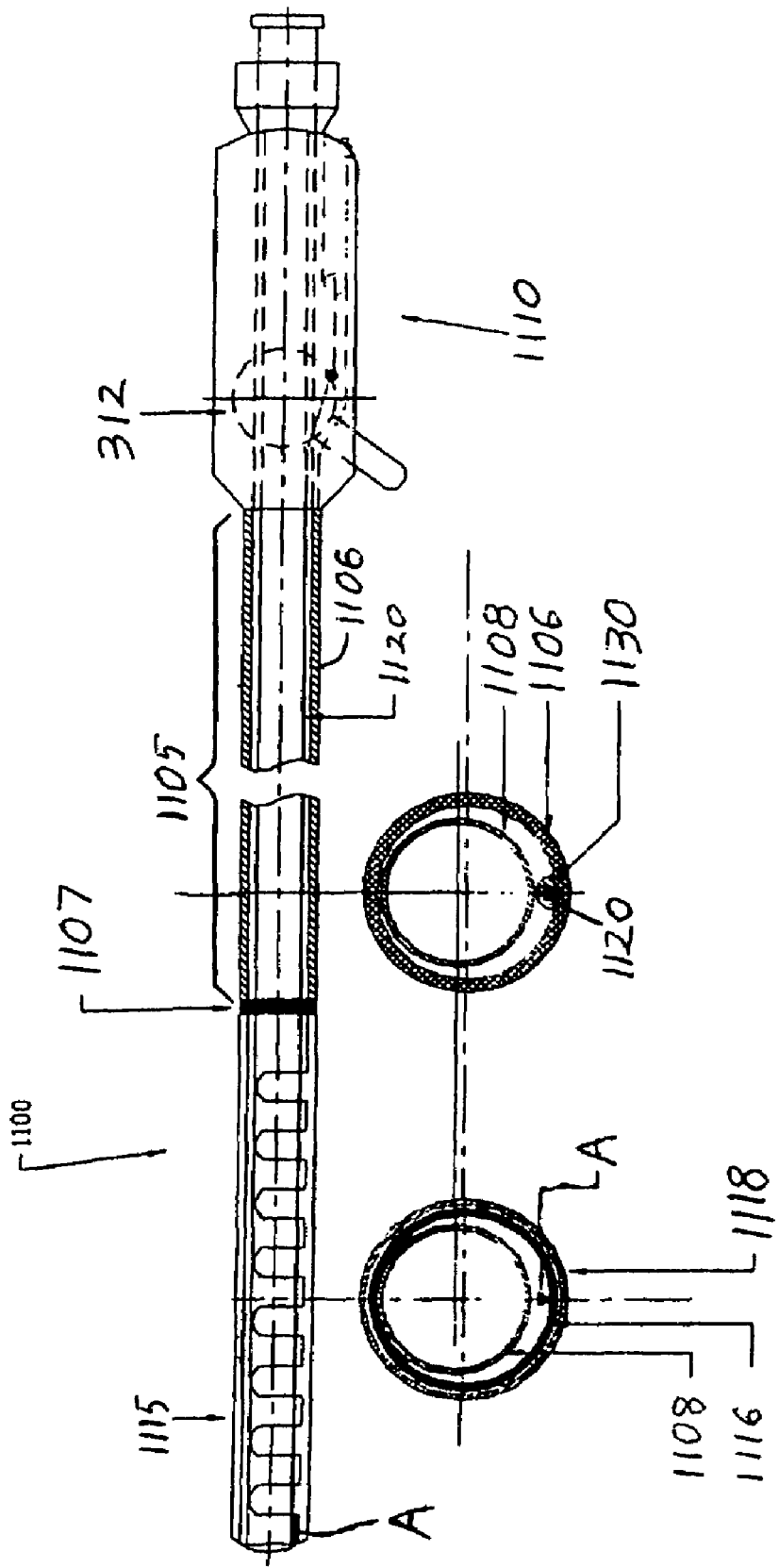
FIG. 11 is a schematic diagram of a uni-directional, deflectable tip guide catheter, in accordance with a sixth exemplary embodiment of the present invention.

The exemplary embodiments described herein below, involve deflectable guide catheters. In general, the guide catheters covered by these embodiments comprise a proximal, non-deflectable shaft and a distal, deflectable tip section. Referring now to FIG. 11, the distal, deflectable tip section 1115 of a guide catheter 1100 preferably includes outer tubing 1118 and, within the outer tubing 1118, thin walled hypotubing 1116, made from a superelastic MRI compatible metal/alloy, such as nitinol, MP35N, and the like. The hypotubing 1116 is slotted (i.e., it has cut-outs) on at least one side, similar to that which is illustrated in FIG. 2. The diameter of the lumen associated with a guide catheter 1100 is relatively large to accommodate the one or more medical instruments passing therethrough. The slotted hypotubing 1116 provides greater deflectability where the diameter of the distal, deflectable tip section 1115 is, as stated, relatively large.

In accordance with the guide catheters in the exemplary embodiments described below, the proximal, non-deflectable shaft portion is preferably covered by braided or non-braided tubing. If braided tubing is used, the braiding material will be a MRI compatible metal, for example, nitinol, tungsten, titanium, tantalum, MP35N, or a non-metal, such as Kevlar. Moreover, these guide catheters may have an inner tubing 1108 running the length of the catheter, where the lumen of this inner tubing would accommodate the aforementioned medical instruments. The inner tubing 1108 will be made from a suitable, MRI compatible material that also facilitates the movement of the one or more medical instruments (e.g., Teflon).

FIG. 11 is a schematic diagram of a uni-directional, deflectable tip guide catheter 1100, in accordance with a sixth exemplary embodiment of the present invention. As set forth above, the deflectable tip guide catheter 1100 includes a proximal, non-deflectable shaft 1105, a handle 1110, and a distal, deflectable tip section 1115. The non-deflectable shaft 1105 is covered, in this embodiment, by braided tubing 1106, where the braiding is made from an MRI compatible material. The distal, deflectable tip section 1115 contains a slotted hypotube 1116. The distal, deflectable tip section 1115 is electrically isolated from the braid 1106 by an insulating strip 1107. In addition, the guide catheter 1100 includes a pull wire 1120. In the non-deflectable shaft 1105, the pull wire 1120 runs along the inside of the braided tubing 1106, within a pull wire tube or lumen 1130, thus creating an eccentric coaxial cable. In the distal, deflectable tip section 1115, the pull wire 1120 runs along the inner wall of the slotted hypotube 1116, and is attached thereto at point A', as shown. In this sixth exemplary embodiment, the braided tubing 1106 and the pull wire 1120 together form a loopless antenna. A matching-tuning circuit, such as the one shown in FIG. 5A, may be used to decouple and tune the loopless antenna and to provide a single RF output signal for the MRI scanner, so the catheter 1100 can be actively tracked and/or visualized.

Further regarding the guide catheter 1100, the braided tubing 1106 and the pull wire 1120 may, alternatively, be configured so as to form an elongated loop antenna, rather than a loopless antenna. In accordance with this alternative embodiment, the braid of the braided tubing 1106 is electrically connected to the proximal end of the slotted hypotube 1116, whereas the insulated pull wire 1120 is connected to the distal end of the slotted hypotube 1116. Both the pull wire 1120 and the braiding of the braided tubing 1106 are connected to the core and the shielding of a coaxial cable (not shown) at the proximal end of the catheter, for example, in the handle of the catheter, wherein an interface circuit, such as the matching-tuning circuit shown in FIG. 10B, is employed to decouple and tune the loop antenna, and to generate and forward an RF output signal to the MRI scanner so that the catheter 1100 can be actively tracked and/or visualized.

Figure 12:
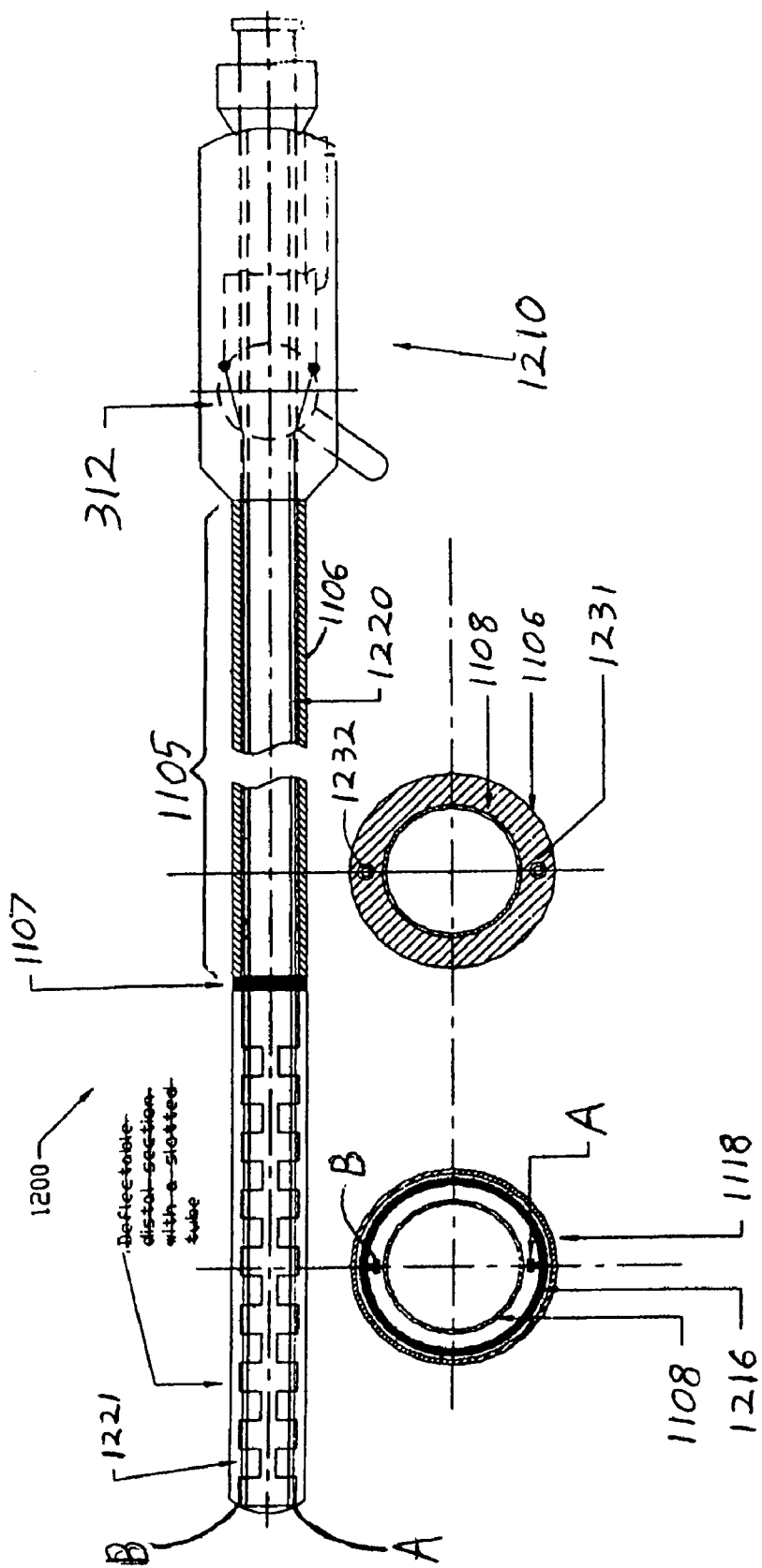
FIG. 12 is a schematic diagram of a bi-directional, deflectable tip guide catheter 1200, in accordance with a seventh exemplary embodiment of the present invention.

FIG. 12 is a schematic diagram of a bi-directional, deflectable tip guide catheter 1200, in accordance with a seventh exemplary embodiment of the present invention. The guide catheter 1200 is substantially similar to the guide catheter 1100, illustrated in FIG. 11, except that guide catheter 1200 has two pull wires 1220 and 1221 that pass within pull wire lumens 1231 and 1232, rather than one pull wire, where the pull wires 1220 and 1221 are attached to the inner wall of the slotted hypotube 1216 at points A and B, respectively, to facilitate bi-directional deflection. In addition, the two pull wires 1220 and 1221 are electrically configured to form a loop antenna. Although not shown in FIG. 12, an interface circuit, such as the matching-tuning circuit 1040 in the handle of catheter 1000, illustrated in FIG. 10, may be employed to decouple and tune the loop antenna, and to provide an RF output signal for the MRI scanner so the catheter 1200 can be actively tracked and/or visualized. It will be understood, however, that the two pull wires 1220 and 1221 could be configured, in the alternative, to form a loopless antenna.

The guide catheters 1100 and 1200, described above, can, of course, be modified such that they may be employed as injection catheters. This may be achieved, for example, by incorporating an injection needle into the guide catheter assembly, where the injection needle can be actively tracked and/or visualized by providing a corresponding, separate RF path between the needle and the MRI scanner via an interface circuit. Alternatively, the needle may also be passively tracked.

Figure 13:
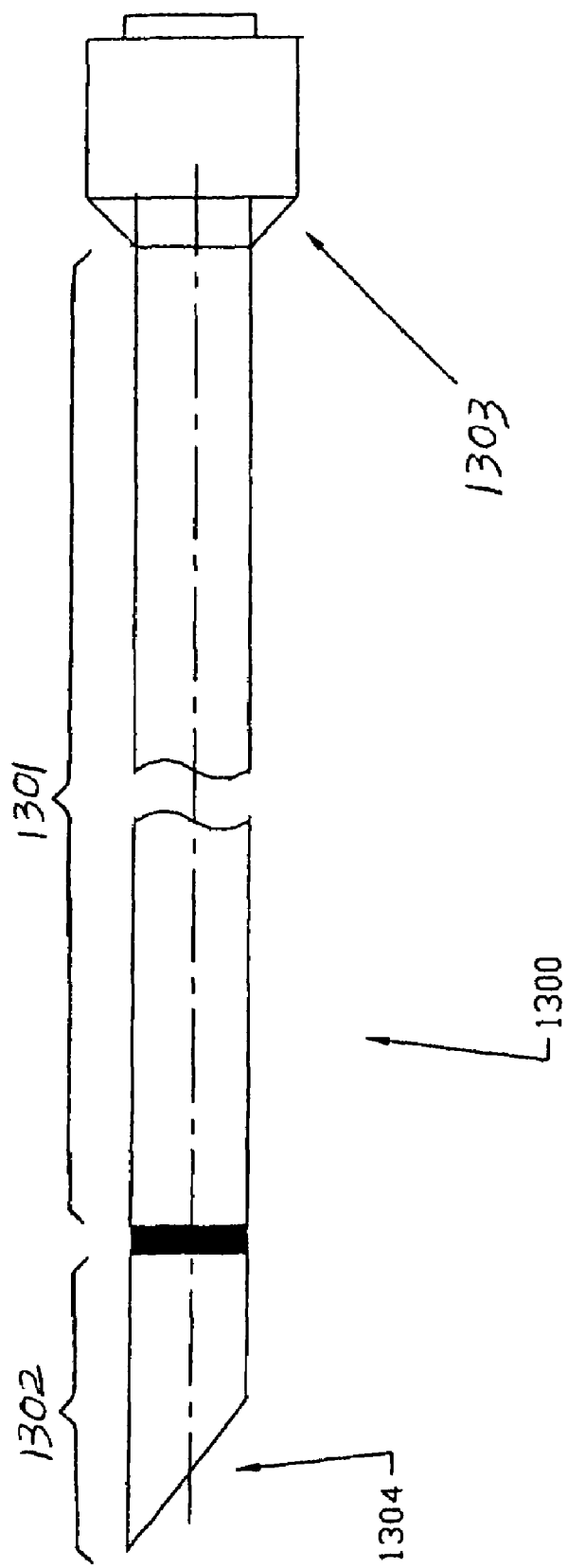
FIG. 13 is a diagram of an injection needle that can be passively tracked in an MRI environment, for use with a deflectable tip injection catheter in accordance with exemplary embodiments of the present invention.

FIG. 13 is a diagram of an injection needle 1300 that can be passively tracked in an MRI environment. As shown, needle 1300 has a proximal, polymeric tube section 1301, a distal section 1302 (comprised, for example, of metal), and a luer 1303. The distal section 1302 is made of an MRI compatible metal, and it includes a beveled tip 1304. The luer 1303 is used to attach a syringe that may contain a therapeutic agent. The length of the needle 1300 will approximate ¼ wavelength ($\lambda$), for example, 10 cm for a 1.5 Tesla system). In addition, the needle 1300 may be insulated or un-insulated. Preferably, there would be some calibrated indicator on the handle, for example, that reflects the extent to which the needle 1300 is deployed in the patient tissue. The primary advantage realized by the use of needle 1300 is that the proximal polymeric section 1301 does not generate any significant heat, which might otherwise pose a safety hazard for the patient.

Figure 14:
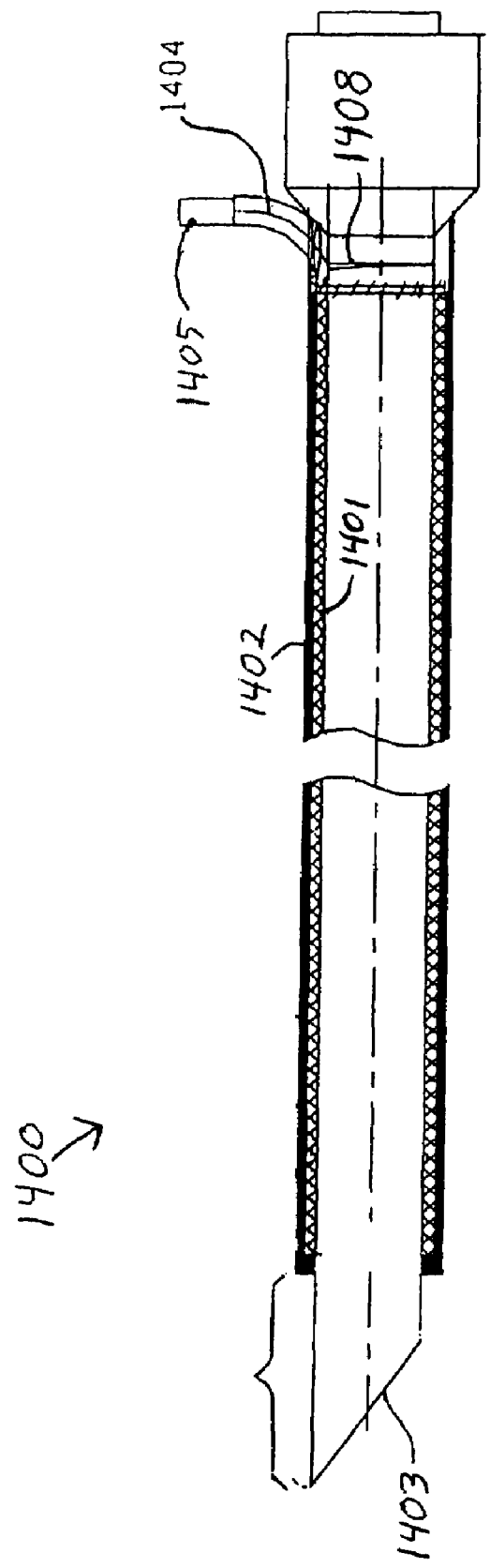
FIG. 14 is a diagram of an injection needle, configured as a loop antenna, capable of being actively tracked in an MRI environment, separately and independently from the catheter, in accordance with exemplary embodiments of the present invention.

FIG. 14 is a diagram of an injection needle 1400 that is capable of being actively tracked, separately and independently from the guide catheter. As shown, the needle 1400 has a proximal section, where the proximal section is covered by an inner shielding layer 1401, and where the inner shielding 1401 is covered by an outer insulating layer 1402. The needle 1400 also has a distal tip portion 1406 with a beveled edge 1403. The distal tip portion 1406 is made from an MRI compatible metal, and it includes a polymeric insulating sheath (not shown). Together, the shielding layer 1401, the outer insulating layer 1402, and the polymeric insulating sheath (not shown) prevent the needle 1400 from generating a significant amount of heat, which might otherwise pose a safety hazard for the patient. In addition, the needle 1400 has a built-in loop antenna 1408, which is connected to an interface circuit via one or more electrical leads 1404 through a BNC connector 1405. It is this built-in antenna that allows the needle 1400 to be actively tracked and/or visualized separate and independent of guide catheter in which the needle 1400 is contained. It should be noted that the needle 1400 may be coated with an insulating polymeric dielectric layer, e.g., polyimide, polyurethane lacquer, and the like, on the inside.

Figure 15:
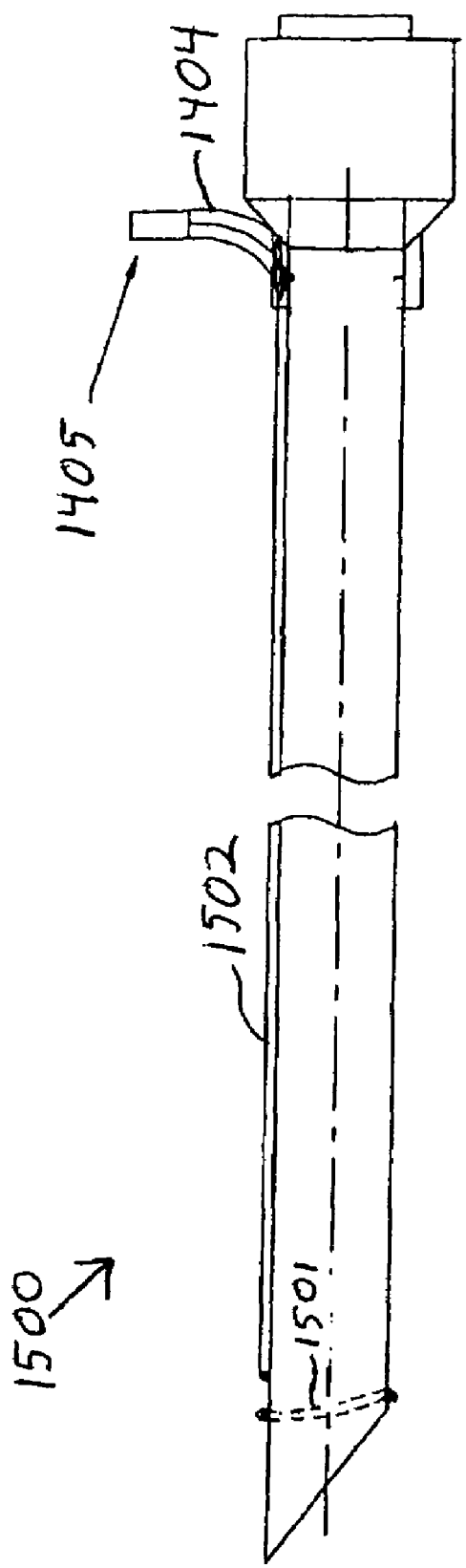
FIG. 15 a diagram of an injection needle, configured as a loopless antenna, capable of being actively tracked in an MRI environment, separately and independently from the catheter, in accordance with exemplary embodiments of the present invention.

FIG. 15 is a diagram of an injection needle 1500 that is capable of being actively tracked, separately and independently from the guide catheter. It differs from the injection needle illustrated in FIG. 14 in that injection needle 1500 is configured as a loopless antenna 1502, rather than a loop antenna 1408.

It is of particular importance to be able to track and/or visualize the distal tip of the injection needle. Thus, the needles described above may include a thin metallic wire 1501 coiled around the distal tip. This will increase the intensity of the RF signal associated with the distal tip of the needle, thereby making the distal tip of the needle more visible under MRI.

The ability to identify and select the geometric plane in which the catheter lies during an MRI procedure is quite important, as it allows the attending physician to then more rapidly and precisely identify and prescribe image slices of interest that are associated with or intersect this plane. U.S. Pat. No. 6,687,530, which is incorporated herein by reference, proposes a methodology for tracking the location of individual coils located along the length of a catheter, in three-dimensional space, using MRI, and acquiring an image in or associated with the geometric plane defined by the location of the coils. This technique then permits an attending physician to identify the geometric plane and, thereafter, select and visualize imaging slices relative to that geometric plane. A catheter in accordance with exemplary embodiments of the present invention will now be described for use with an MRI system that employs the capability provided by this or similar methodologies.

Figure 16:
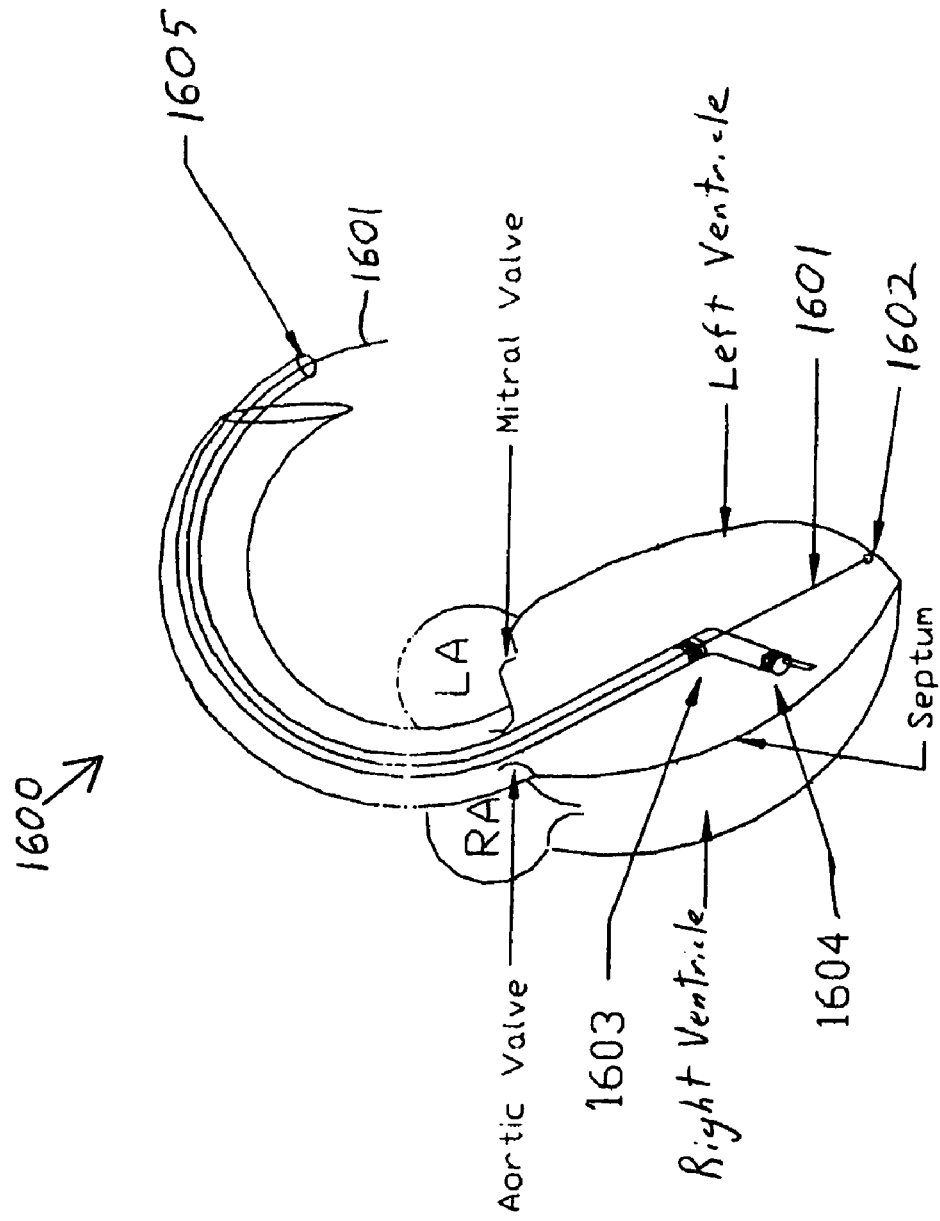
FIG. 16 a schematic diagram of a deflectable tip catheter, in accordance with an eighth exemplary embodiment of the present invention.

FIG. 16 is a diagram of a deflectable tip catheter 1600, that includes three individual inductor loop coils, in accordance with an eighth exemplary embodiment of the present invention, wherein the basic structure and design of the deflectable tip catheter 1600 may take the form of any one of the catheters described in the previous exemplary embodiments, with the addition of a guidewire lumen 1605. The deflectable tip catheter 1600 has, in addition to those catheters described above, a guidewire 1601, which is made from a relatively stiff, MRI compatible material. Attached to or connected to the distal tip of the guidewire 1601 is an inductor loop coil 1602. The attending physician will advance the guidewire 1601 into the left ventricle or other anatomical structure of interest, as shown in FIG. 16. The attending physician then advances the deflectable tip catheter 1600 over the guidewire 1601, where the guidewire 1601 runs through a guidewire lumen 1605. There are two additional inductor loop coils 1603 and 1604 located at the deflectable tip section of the catheter 1600. More specifically, coil 1603 is located at the fulcrum, or point of deflection, and coil 1604 is located at the distal tip of the catheter 1600.

Each of the three inductor loop coils 1602, 1603 and 1604 are electrically connected to a corresponding coaxial cable (not shown) so that the MRI system using, for example, the aforementioned software, can identify the location of the three inductor loop coils 1602, 1603, and 1604 in three dimensional space within the anatomical structure of interest, track the geometric plane through the anatomical structure of interest defined by the location of the three coils 1602, 1603, and 1604, and generate an image slice relative to the geometric plane as specified by the attending physician. Once the attending physician has positioned the distal tip of deflectable catheter 1600 so that it is pointing towards the region of interest, the physician may advance the injection needle into, for example, the myocardial tissue to deliver a therapeutic agent.

Figure 17:
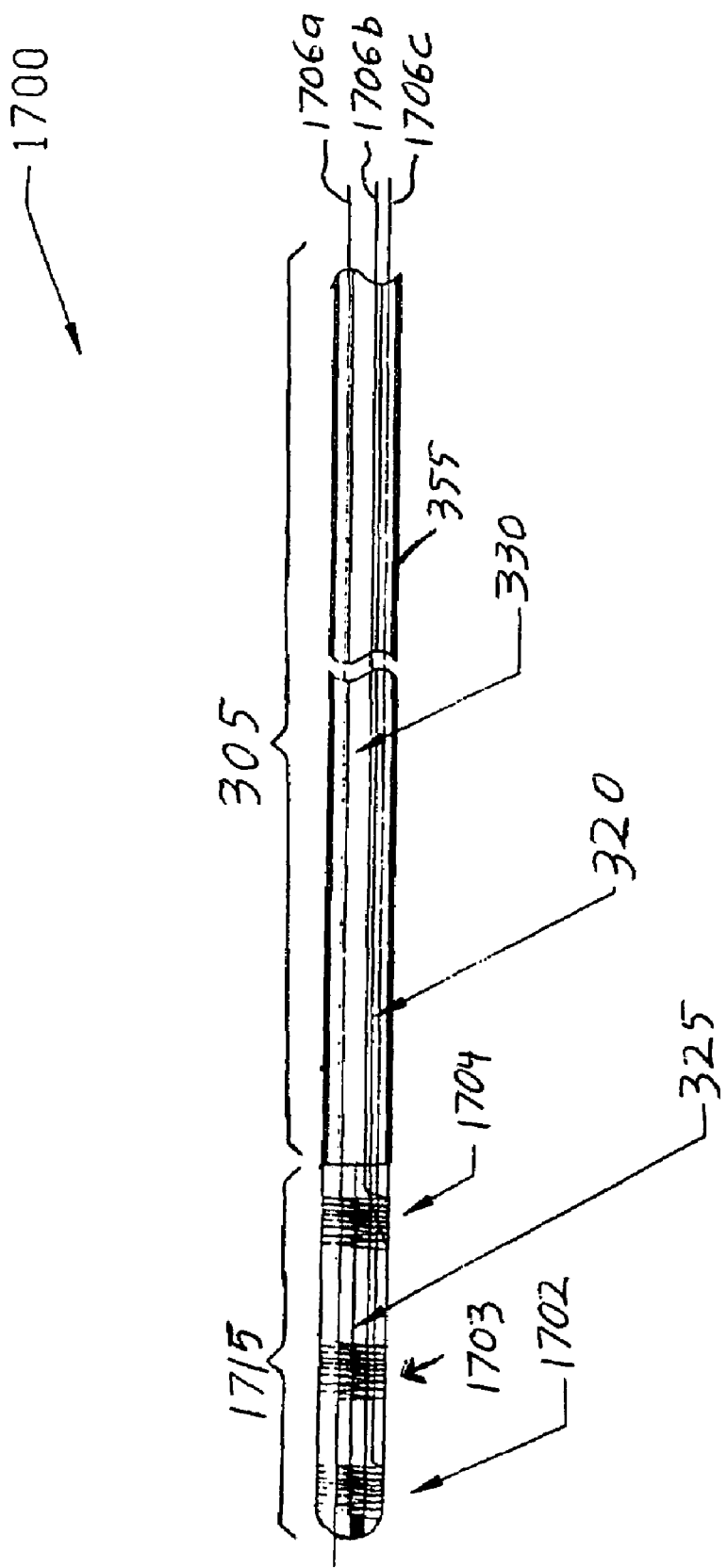
FIG. 17 is a schematic diagram of a deflectable tip catheter, including three, non-magnetic inductor loop coils, in accordance with exemplary embodiments of the present invention.

FIG. 17 is a schematic diagram of a deflectable tip catheter 1700, including three, non-magnetic inductor loop coils, in accordance with an alternative to the eighth exemplary embodiment described above. As shown, the three inductor loop coils 1702, 1703, and 1704 are built into the distal, deflectable tip section 1715. Each of the inductor loop coils 1702, 1703, and 1704 are electrically connected to a corresponding center conductor 1706a, 1706b, and 1706c, respectively, of a coaxial cable (not shown), so that the MRI scanner, through, for example, software as described above, can individually identify the position and/or location of each coil in three dimensional space and, there from, acquire an image associated with the geometric plane defined by the position of the three coils. This information will assist the attending physician in guiding or steering the catheter 1700 into a desired location and/or position.

These individual loop coils could be coiled circumferentially around the diameter of the catheter, on the outside or inside of the catheter tubing. In addition, the coils may be placed inside the distal tip, or other locations, and oriented in the x, y and z planes, i.e., orthogonal to one another. The aforementioned tracking methodology could be implemented to track the position and location of the coils.

Figure 18:
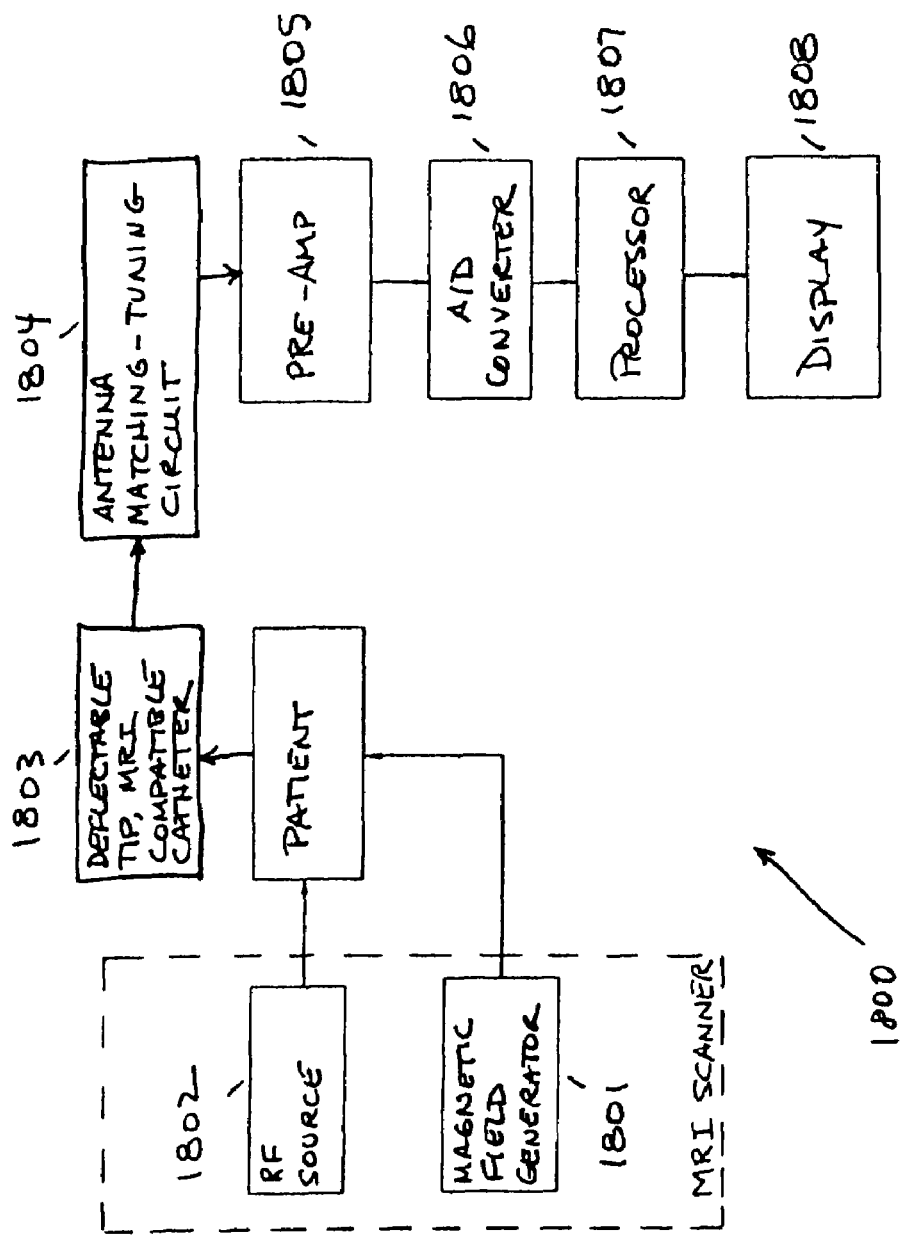
FIG. 18 is a schematic diagram of an MRI system, including a deflectable tip, MRI compatible catheter, in accordance with exemplary embodiments of the present invention.

FIG. 18 is a diagram of an MRI system 1800 in accordance with exemplary embodiments of the present invention. The MRI system 1800 of FIG. 18 includes a magnetic field generator 1801, for establishing a magnetic field on the patient, and an RF source 1802 for emitting RF signals to at least a portion of the patient disposed within the magnetic field. Of particular importance, the MRI system 1800 employs a deflectable tip, MRI compatible catheter 1803, in accordance with the present invention, such as any of the deflectable tip catheters described herein above. In addition, the MRI system 1800 includes an interface circuit 1804. The specific antenna interface circuit that is employed will, of course, depend on the deflectable tip, MRI compatible catheter 1803 that is employed, as set forth above. The RF signals received by the antenna in the deflectable tip MRI compatible catheter 1803 and the antenna interface circuit 1804 are then amplified by the pre-amplifier 1805, and converted from analog to digital by the A/D converter 1806. The digital signals are then provided to the processor 1807, which employs hardware and/or software, as discussed above) to generate MRI information relating to the patient, as well as the position and location of the deflectable tip, MRI compatible catheter 1803 and, in accordance with certain embodiments described above, the position and location of any surgical instrument or instruments contained in the catheter 1803 (e.g., the position and location of an injection needle). The MRI information is then displayed in the form of a MR image on display 1808, so that the attending physician can visualize and more effectively steer the catheter 1803 to or within the anatomical structure of interest.

It will be apparent to those skilled in the art that various modifications and variations of the exemplary embodiments described above can be made without departing from the spirit or scope of the present invention. Thus, it is intended that the present invention cover these modifications and variations provided they come within the scope of the appended claims and the equivalents thereof.

What is claimed is:

1. An MRI system comprising:
an MRI scanner;

an MRI catheter antenna sized and configured as an intramyocardial catheter, comprising:
  a non-deflectable section;
  a controllably deflectable section having a proximal end abutting a distal end of the non-deflectable section at an interface, wherein the deflectable section includes a deflectable tip;
  a first lumen extending from a proximal end of the non-deflectable section toward the deflectable section;
  an electrically conductive pull wire extending from the proximal end of the non-deflectable section toward the deflectable section, wherein the pull wire travels within the first lumen and is coupled at its distal end to a distal portion of an interior wall of the deflectable section;
  a second lumen, separate from the first lumen, extending from the proximal end of the non-deflectable section toward the deflectable section;
  an electrically conductive first injection needle, having a distal sharpened tip, extending from the proximal end of the non-deflectable section toward the deflectable section, wherein the first injection needle travels within the second lumen and the distal sharpened tip protrudes from or withdraws into an interior space of the deflectable section during use inside a patent's heart;
  an electrical connector in communication with the MRI scanner and the catheter antenna; and
  an electrical connection between the electrically conductive pull wire and the electrically conductive first injection needle, wherein the electrical connection forms a common electrical node between the pull wire and the first injection needle.

2. The MRI system of claim 1, wherein the pull wire and the needle extend in a parallel orientation in a longitudinal direction inside the first and second lumens of the catheter antenna and each define an internal core of the catheter antenna.

3. The MRI system of claim 1, further comprising:
  an anchor wire anchored at a first end to the interface and coupled at a second end, distal to the first end, to the distal portion of the interior space of the deflectable section.

4. The MRI system of claim 1, wherein the first injection needle has a distal end comprising a MRI compatible metal that defines the sharpened tip, and wherein the distal end merges upstream thereof into a non-metallic polymeric portion.

5. The MRI system of claim 1, wherein the first injection needle has a distal end that has increased flexibility relative to a proximal end thereof.

6. The MRI system of claim 1, wherein the first injection needle comprises a thin coiled wire residing about a distal portion thereof to increase MRI signal intensity obtained by the catheter antenna or needle.

7. The MRI system of claim 1, further comprising an insulated metallic wire connected to one of the first injection needle or the pull wire at the distal end portion of the catheter antenna.

8. The MRI system of claim 1, the catheter antenna further comprises a luer at a proximal portion thereof in communication with the first injection needle.

9. The MRI system of claim 1, the catheter antenna comprising a second needle that is extendable from a distal end portion of the catheter antenna independently of the first needle, and wherein the first and second needles define separate cores of the catheter antenna.

10. The MRI system of claim 1, wherein the catheter antenna is a loopless antenna, and wherein the pull wire defines a first core of the catheter antenna and the needle or a different surgical instrument defines a second core of the catheter antenna.

11. The MRI system of claim 1, wherein a distal end portion of the deflectable section of the catheter antenna includes a side exit aperture that allows the injection needle to exit a side of the catheter antenna.

12. The MRI system of claim 1, further comprising a handle connected to a proximal end of the non-deflectable section and housing a deflection dial functionally coupled to the pull wire to controllably deflect the deflectable section.

13. The MRI system of claim 12, wherein the catheter antenna is configured as a loopless antenna.

14. The MRI system of claim 12, wherein the catheter antenna is configured as a loop antenna.

15. The MRI system of claim 1 further comprising:
  means for processing RF signals received from the catheter antenna.

16. The MRI system of claim 15 further comprising:
  means for tracking the deflectable tip of the catheter antenna inside a patient based on the processed RF signals received from the antenna.

17. The MRI system of claim 15 further comprising:
  means for visualizing the catheter antenna inside a patient based on the processed RF signals received from the catheter antenna.

18. The MRI system of claim 15, wherein the deflectable tip of the catheter antenna comprises a plurality of inductor loop coils, and wherein the processing means comprises:
  means for determining a location within a patient for each of the inductor loop coils; and
  means for identifying an image slice, in three dimensional space, as a function of the location of the inductor loop coils.

19. A magnetic resonance imaging method comprising the steps of:
  generating a magnetic field around at least a portion of a patient;
  transmitting RF energy over a portion of the patient exposed to the magnetic field;
  receiving the RF energy using a catheter antenna located in the patient, the catheter antenna comprising:
    a non-deflectable section;
    a controllably deflectable section having a proximal end abutting a distal end of the non-deflectable section at an interface, wherein the deflectable section includes a deflectable tip;
    a first lumen extending from a proximal end of the non-deflectable section toward the deflectable section;
    an electrically conductive pull wire extending from the proximal end of the non-deflectable section toward the deflectable section, wherein the pull wire travels within the first lumen and is coupled at its distal end to a distal portion of a wall associated with an interior space of the deflectable section;
    a second lumen, separate from the first lumen, extending from the proximal end of the non-deflectable section toward the deflectable section;
    an electrically conductive needle, having a distal sharpened tip, extending from the proximal end of the non-deflectable section toward the deflectable section, wherein the needle travels within the second lumen and the distal sharpened tip protrudes from or withdraws into the interior space of the deflectable section;

an electrical connector in communication with the MRI scanner and the catheter antenna;

an electrical connection between the electrically conductive pull wire and the electrically conductive needle, wherein the electrical connection forms a common electrical node between the pull wire and the needle; and generating a magnetic resonance image that includes a visualization of the catheter antenna deflectable tip in the patient.

20. The method of claim 19 further comprising the step of:

steering the deflectable tip of the catheter antenna to a location of interest in the patient using the image that includes the visualization of the deflectable tip of the catheter antenna.

21. The method of claim 20, wherein the electrically conductive needle is sized and configured as an intramyocardial injection needle, said method further comprising the step of:

injecting a therapeutic agent into intramyocardial tissue of the patient using the injection needle.

22. The method of claim 19, wherein the catheter antenna further comprises:

an anchor wire anchored at a first end to the interface and coupled at a second end, distal to the first end, to the distal portion of the interior space of the deflectable section, the method further comprising the step of limiting a deflection of the deflectable tip using the anchor wire to restrain the pull wire.

* * * * *